(12) United States Patent
Usher et al.

(10) Patent No.: US 7,097,690 B2
(45) Date of Patent: Aug. 29, 2006

(54) APPARATUS AND METHOD FOR REMOVING GASSES FROM A LIQUID

(75) Inventors: Kathryn M. Usher, Saratoga, NY (US); George R. Foster, Glen Falls, NY (US); Edward M. Kolvek, West Newbury, MA (US); Andrew C. Harvey, Waltham, MA (US); Malcolm E. Taylor, Pepperell, MA (US); Thomas Williams Lovell, Beverly, MA (US); Colin P. Hart, Queensbury, NY (US); William Edmund Girzone, Saratoga Springs, NY (US)

(73) Assignee: Scimed Life Systems, Inc., Maple Grove, MN (US)

( * ) Notice: Subject to any disclaimer, the term of this patent is extended or adjusted under 35 U.S.C. 154(b) by 221 days.

(21) Appl. No.: 10/684,215

(22) Filed: Oct. 10, 2003

(65) Prior Publication Data

US 2005/0077225 A1    Apr. 14, 2005

(51) Int. Cl.
*C02F 1/44* (2006.01)
*B01D 53/22* (2006.01)

(52) U.S. Cl. .............. 95/46; 96/6; 96/7; 96/8; 96/10; 96/14; 604/9; 604/122; 604/126

(58) Field of Classification Search ............ 95/46; 96/6–8, 10, 14; 604/9, 49, 122, 126
See application file for complete search history.

(56) References Cited

U.S. PATENT DOCUMENTS

| | | | |
|---|---|---|---|
| 3,668,837 A * | 6/1972 | Gross ............................. | 96/6 |
| 3,735,562 A * | 5/1973 | Mousseau et al. ............ | 96/6 |
| 3,782,382 A | 1/1974 | Naftulin et al. | |
| 3,827,562 A * | 8/1974 | Esmond ..................... | 210/304 |
| 4,033,345 A | 7/1977 | Sorenson et al. | |
| 4,127,481 A | 11/1978 | Malchesky et al. | |
| 4,200,096 A | 4/1980 | Charvin | |
| 4,219,422 A | 8/1980 | Knothe et al. | |
| 4,280,495 A | 7/1981 | Lampert | |
| 4,324,239 A | 4/1982 | Gordon | |
| 4,326,957 A | 4/1982 | Rosenberg | |
| 4,345,919 A | 8/1982 | Wilkinson et al. | |
| 4,395,260 A | 7/1983 | Todd et al. | |
| 4,447,230 A | 5/1984 | Gula et al. | |
| 4,568,327 A | 2/1986 | Seufert | |
| 4,568,333 A | 2/1986 | Sawyer et al. | |
| 4,571,244 A | 2/1986 | Knighton | |

(Continued)

FOREIGN PATENT DOCUMENTS

EP       0 448 973       10/1991

(Continued)

*Primary Examiner*—Jason M. Greene
(74) *Attorney, Agent, or Firm*—Crompton, Seager & Tufte, LLC

(57) ABSTRACT

Medical devices for removing gasses, such as gas bubbles and/or dissolved gasses, from a liquid to be delivered to a patient, and methods of use and making of such devices. In at least some embodiments, a gas permeable membrane material is used in the construction of the gas removal devices. In some embodiments, layers of gas permeable membrane material are used to construct a filter structure for removing gas from the liquid. In other embodiments, hollow tubes and/or fibers of the gas permeable membrane material are used to construct a filter structure for removing gas from the liquid. The gas removal devices may be used in any of a broad variety of liquid delivery systems and/or configurations.

60 Claims, 14 Drawing Sheets

U.S. PATENT DOCUMENTS

| | | | |
|---|---|---|---|
| 4,572,724 A | 2/1986 | Rosenberg et al. | |
| 4,599,093 A * | 7/1986 | Steg, Jr. | 95/46 |
| 4,636,313 A | 1/1987 | Vaillancourt | |
| 4,642,089 A | 2/1987 | Zupkas et al. | |
| 4,643,713 A | 2/1987 | Viitala | |
| 4,661,096 A | 4/1987 | Teeple | |
| 4,676,771 A | 6/1987 | Henke | |
| 4,684,364 A | 8/1987 | Sawyer et al. | |
| 4,690,762 A | 9/1987 | Katsura | |
| 4,705,497 A | 11/1987 | Shitaokoshi et al. | |
| 4,722,725 A | 2/1988 | Sawyer et al. | |
| 4,734,269 A | 3/1988 | Clarke et al. | |
| 4,806,135 A | 2/1989 | Siposs | |
| 4,834,108 A | 5/1989 | Vaillancourt | |
| 4,872,813 A | 10/1989 | Gorton et al. | |
| 5,049,146 A | 9/1991 | Bringham et al. | |
| 5,061,297 A * | 10/1991 | Krasberg | 95/1 |
| 5,071,404 A | 12/1991 | Larkin et al. | |
| 5,230,862 A * | 7/1993 | Berry et al. | 422/48 |
| 5,238,735 A | 8/1993 | Nagou et al. | |
| 5,249,579 A | 10/1993 | Hobbs et al. | |
| 5,263,982 A | 11/1993 | Shimomura et al. | |
| 5,312,352 A | 5/1994 | Leschinsky et al. | |
| 5,328,463 A | 7/1994 | Barton et al. | |
| 5,346,470 A | 9/1994 | Hobbs et al. | |
| 5,356,375 A | 10/1994 | Higley | |
| 5,382,232 A | 1/1995 | Hague et al. | |
| 5,411,705 A | 5/1995 | Thor et al. | |
| 5,423,751 A | 6/1995 | Harrison et al. | |
| 5,429,595 A | 7/1995 | Wright, Jr. et al. | |
| 5,439,448 A | 8/1995 | Leschinsky et al. | |
| 5,471,244 A | 11/1995 | Wolfe | |
| 5,533,389 A | 7/1996 | Kamen et al. | |
| 5,569,208 A | 10/1996 | Woelpper et al. | |
| 5,580,349 A | 12/1996 | Thor et al. | |
| 5,591,334 A | 1/1997 | Shimizu et al. | |
| 5,593,385 A | 1/1997 | Harrison et al. | |
| 5,616,124 A | 4/1997 | Hague et al. | |
| 5,628,908 A | 5/1997 | Kamen et al. | |
| 5,634,905 A | 6/1997 | Rudolph, Jr. | |
| 5,674,397 A | 10/1997 | Pawlak et al. | |
| 5,695,489 A | 12/1997 | Japuntich | |
| 5,730,712 A | 3/1998 | Falkvall et al. | |
| 5,770,073 A | 6/1998 | Bach et al. | |
| 5,830,261 A * | 11/1998 | Hamasaki et al. | 96/6 |
| 5,863,421 A | 1/1999 | Peter, Jr. et al. | |
| 5,888,275 A * | 3/1999 | Hamasaki et al. | 96/6 |
| 5,899,873 A | 5/1999 | Jones et al. | |
| 5,935,105 A | 8/1999 | Manning et al. | |
| 5,980,742 A * | 11/1999 | Saitoh | 210/198.2 |
| 6,013,061 A | 1/2000 | Kelley | |
| 6,017,493 A | 1/2000 | Cambron et al. | |
| 6,106,715 A * | 8/2000 | Thalmann et al. | 210/321.83 |
| 6,168,648 B1 | 1/2001 | Ootani et al. | |
| 6,248,157 B1 * | 6/2001 | Sims et al. | 96/6 |
| 6,267,926 B1 | 7/2001 | Reed et al. | |
| 6,367,634 B1 | 4/2002 | Lynn et al. | |
| 6,402,818 B1 * | 6/2002 | Sengupta | 96/6 |
| 6,402,821 B1 | 6/2002 | Matsuyama | |
| 6,503,225 B1 | 1/2003 | Kirsch et al. | |
| 6,537,495 B1 | 3/2003 | Cambron et al. | |
| 6,601,710 B1 | 8/2003 | Calhoun et al. | |

FOREIGN PATENT DOCUMENTS

| | | |
|---|---|---|
| WO | WO 93/10889 A1 * | 6/1993 |
| WO | WO 99/32186 | 7/1999 |

* cited by examiner

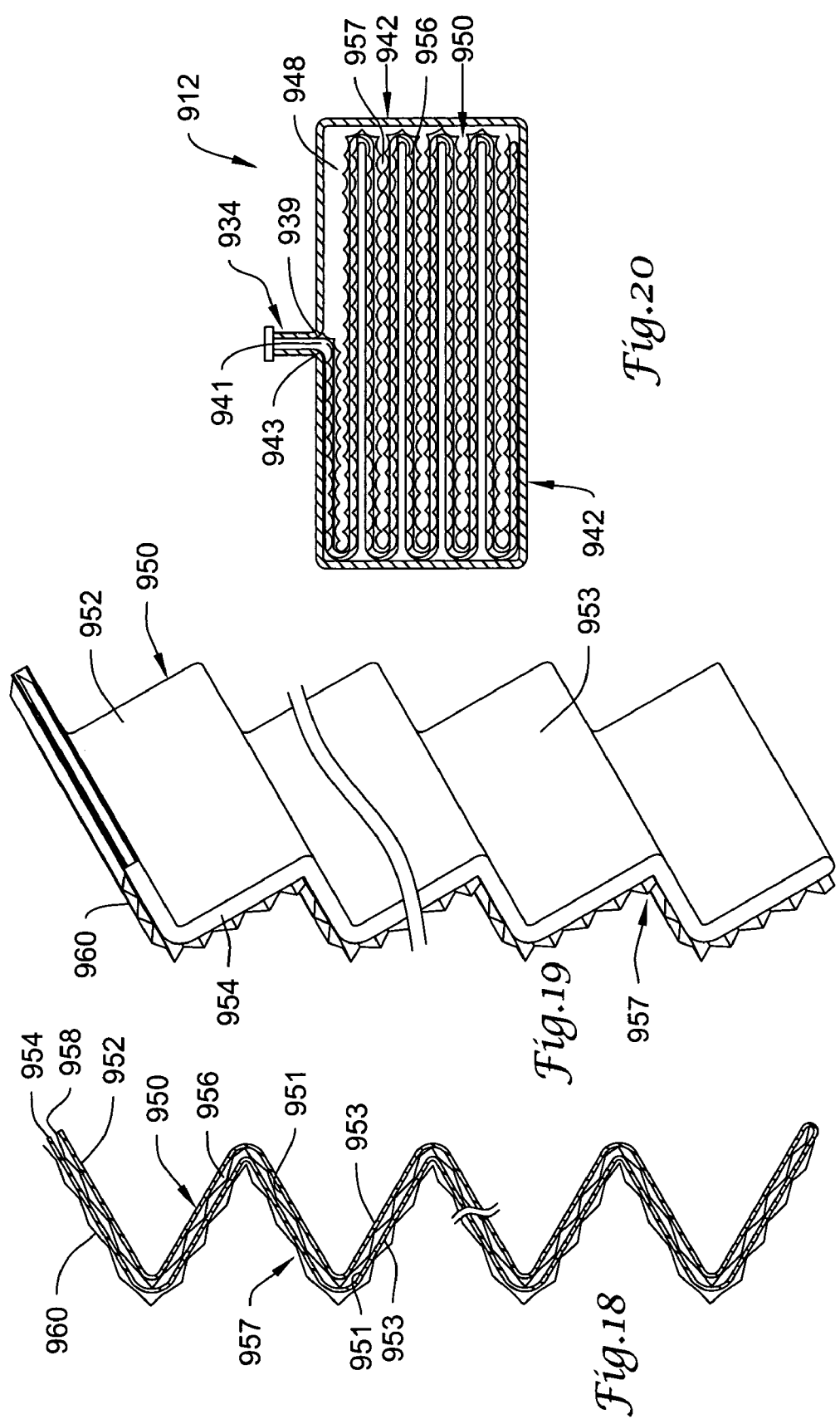

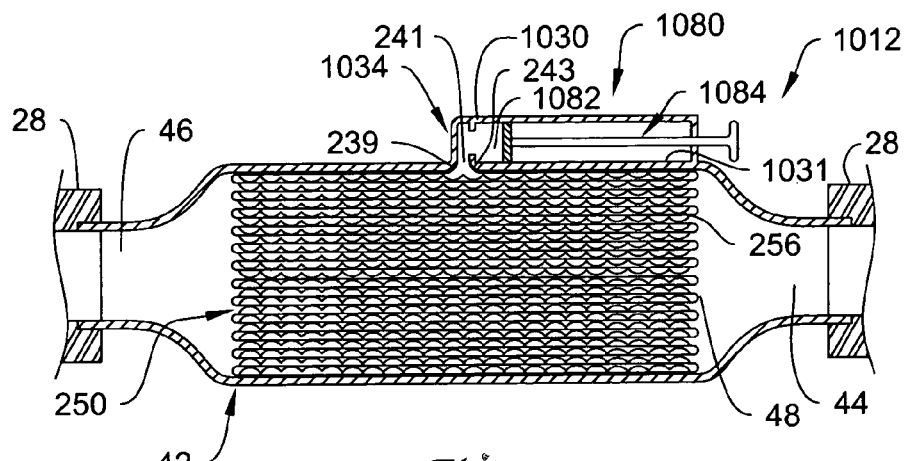
*Fig.21*
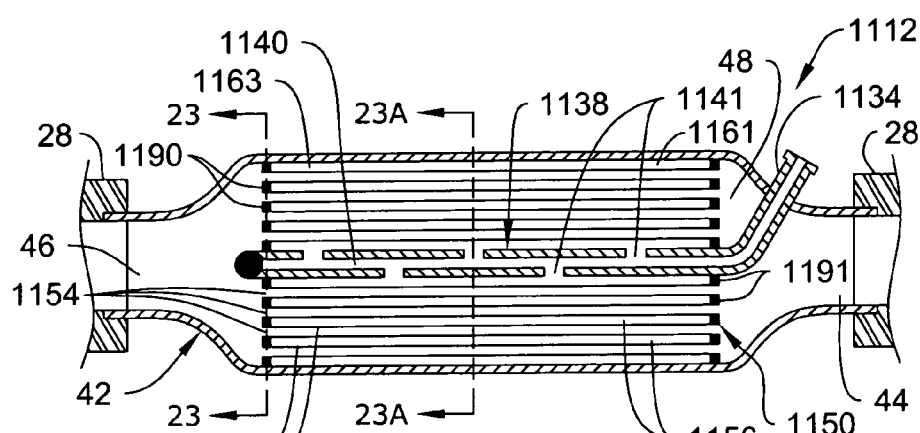
*Fig.22*
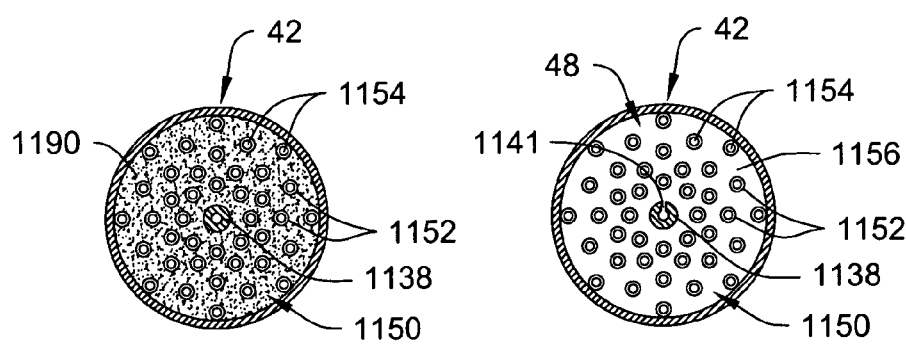
*Fig.23*     *Fig.23A*

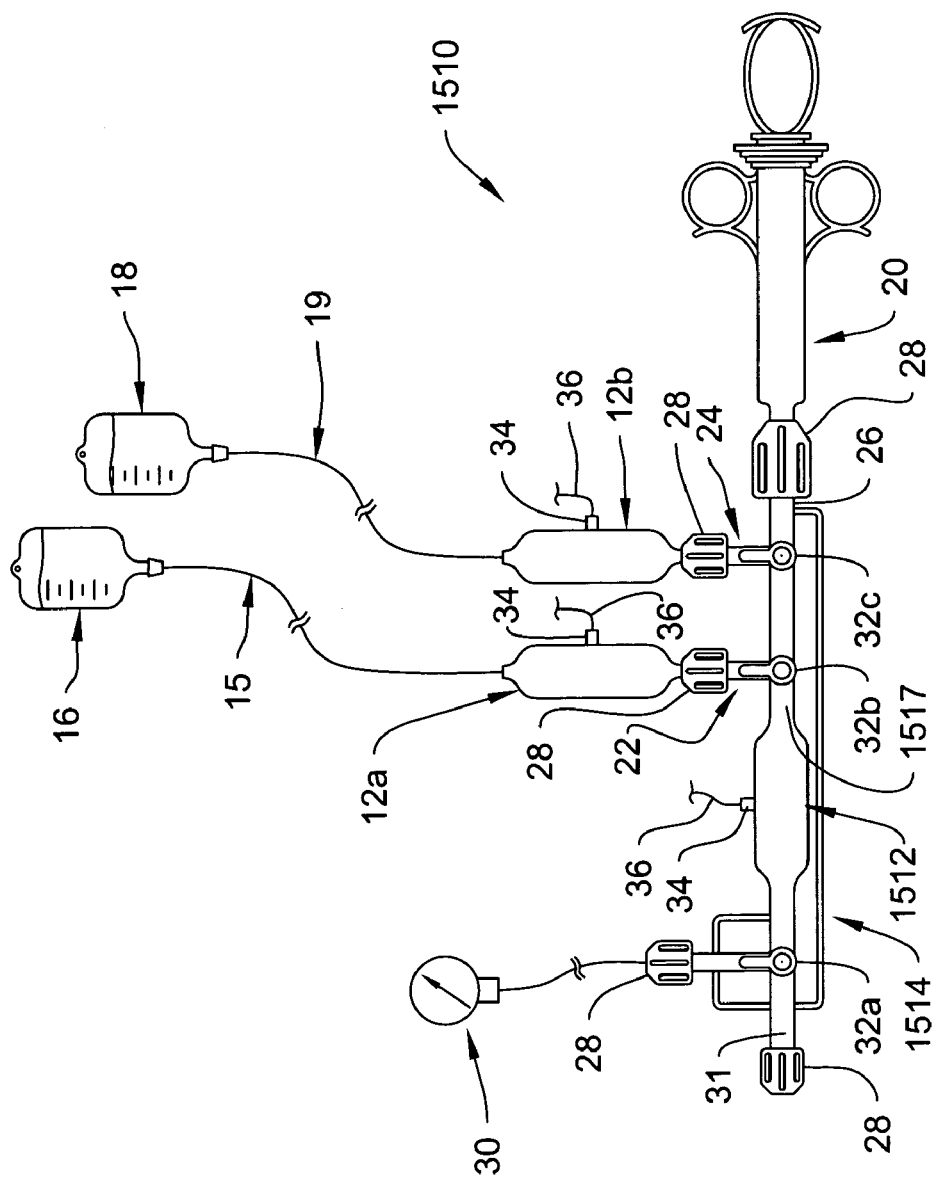

APPARATUS AND METHOD FOR REMOVING GASSES FROM A LIQUID

FIELD OF THE INVENTION

The invention relates to the medical devices and methods of treatment using medical devices, and more particularly the invention relates to devices and methods of removing gasses, such as gas bubbles and/or dissolved gasses, from a liquid to be delivered to a patient.

BACKGROUND

Many diseases and/or conditions are commonly treated and/or diagnosed by procedures involving the introduction of one or more fluids to an internal site within a patient. For example, liquids such as drugs, marker dies, saline, flush solutions, intravenous nutrients, anesthetics, blood, and/or a broad variety of other such liquids may be delivered to an internal site in a patient. For example, the delivery of liquids to a treatment site may be used in procedures such as angioplasty, angiography, catheterization, arterial pressure monitoring, intravenous, interarterial, intercranial or other such delivery procedures, or the like.

In order to prevent or minimize the risk of injury to the patient from air embolism, it is generally necessary to reduce and/or eliminate air or other gasses from the fluid delivered. In many procedures, fluid delivery devices and lines are manually cleared of visible air bubbles by flushing prior to use.

There are a number of different structures and assemblies, and method for use thereof, for removing gasses from a liquid, each having certain advantages and disadvantages. However, there is an ongoing need to provide alternative structures, assemblies, and methods for removing gasses, such as gas bubbles and/or dissolved gasses, from a liquid to be delivered to a patient.

SUMMARY

In some aspects, the invention relates to several alternative designs, materials, and methods of manufacturing alternative structures and assemblies, and alternative methods of removing gasses, such as gas bubbles and/or dissolved gasses, from a liquid to be delivered to a patient.

The above summary is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 9 is a side view of another example embodiment of a catheter infusion system including a plurality of gas removal devices, one of which includes structure for allowing insertion of a device there through;

FIG. 18 is a partial cross-sectional view of a filter assembly used in another example filter device, showing generally folds in the filter assembly prior to insertion into a filter housing;

FIG. 19 is a partial perspective view of the filter assembly of FIG. 18, showing the filter assembly prior to insertion into a filter housing;

FIG. 20 is a partial cross-sectional view taken along a vertical line perpendicular to a longitudinal axis of another example embodiment of a gas removal device (for example, a view similar to the one shown in FIG. 3);

FIG. 21 is a partial cross-sectional side view of another example embodiment of a gas removal device similar to the one shown in FIG. 7, but also including a vacuum generating device on the housing and in fluid communication with the vent port of the gas removal device;

FIG. 22 is a partial cross-sectional side view of another example embodiment of a gas removal device including a plurality of gas permeable hollow fiber membranes and including a central venting configuration;

FIG. 23 is a partial cross-sectional view of the gas removal devices of FIG. 22 taken along line 23—23 of FIG. 22;

FIG. 23A is a partial cross-sectional view of the gas removal devices of FIG. 22 taken along line 23A—23A of FIG. 22;

FIG. 27 is a side view of another example embodiment of a catheter infusion system including a manifold device including a filter structure within the catheter body.

Figure 1:
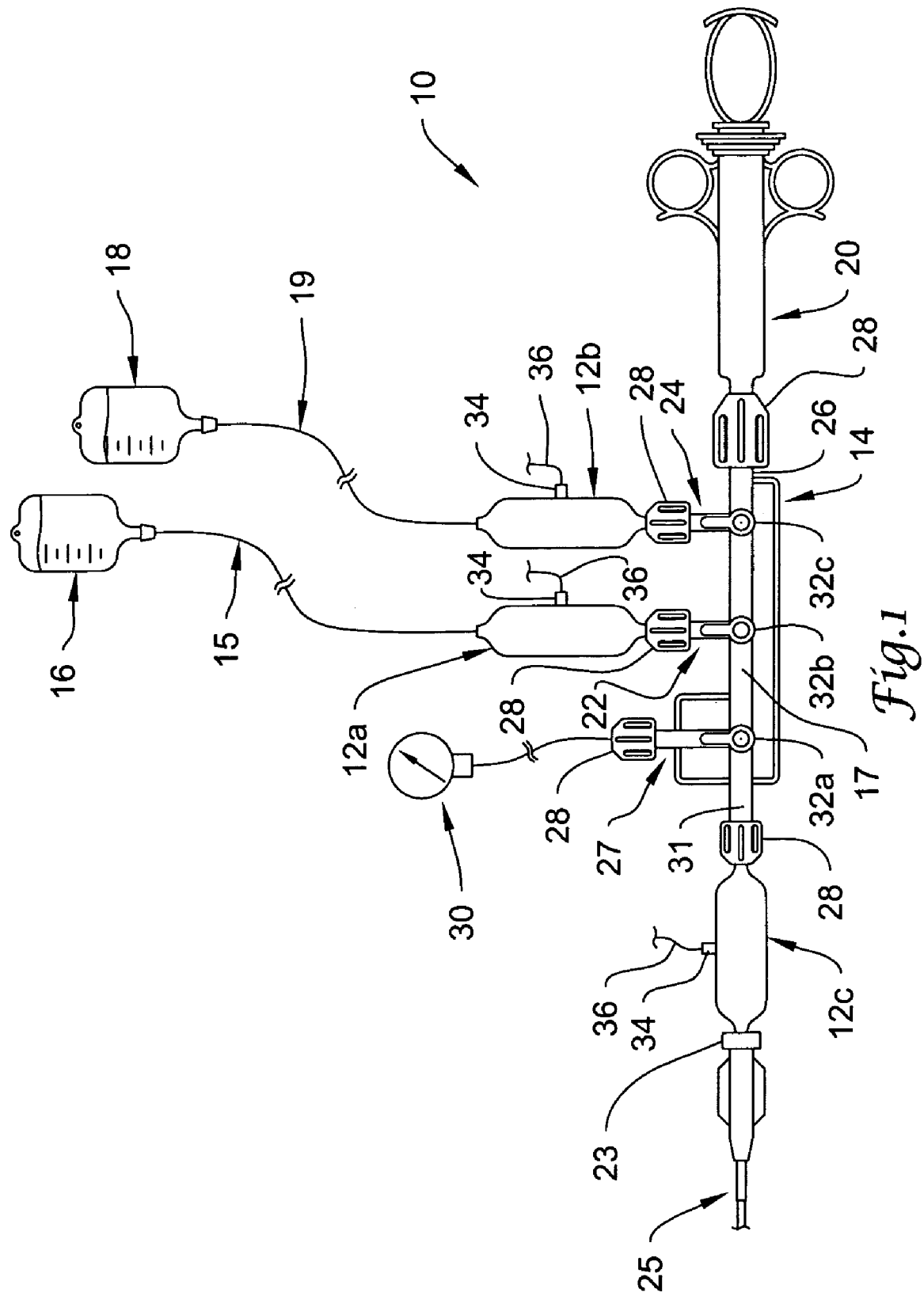
FIG. 1 is a side view of an example embodiment of a catheter infusion system including a plurality of gas removal devices.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description of some example embodiments should be read with reference to the drawings, wherein like reference numerals indicate like elements throughout the several views. The drawings, which are not necessarily to scale, depict some example embodiments and are not intended to limit the scope of the invention. Those skilled in the art and others will recognize that many of the examples provided have suitable alternatives which may also be utilized.

The invention relates to the use of gas permeable membrane material in the construction of gas removal devices adapted and/or configured to remove gas, such as gas bubbles and/or dissolved gas, from a liquid to be delivered to a patient during a medical procedure. In some embodiments, layers of gas permeable membrane material are used to construct a filter structure for removing gas from the liquid. In other embodiments, hollow tubes and/or fibers of the gas permeable membrane material are used to construct a filter structure for removing gas from the liquid. The gas removal devices may be used in any of a broad variety of liquid delivery systems and/or configurations. For example, the gas removal devices may be put into fluid communication with a liquid path of any of a broad variety of liquid delivery structures, either individually or within a system. Some examples of such liquid delivery structures that may be used individually, or within a system, include catheters, hypotubes, syringes, pumps, tubes, lines, manifolds, or any of a broad variety of other liquid delivery structures. A number of example embodiments of gas removal devices and examples of liquid delivery structures, assemblies, and systems are set fourth below. However, it should be noted that the particular embodiments shown and described are given by way of example only.

One example embodiment of a liquid delivery system is shown in FIG. 1. FIG. 1 is a side view of an example infusion system 10 including one or more, and in this case, a plurality of gas removal devices 12a–c. In this particular embodiment, the infusion system is a catheter infusion system including a catheter 25, a manifold 14, and one or more liquid supply containers or reservoirs 16 and 18. The system 10 may also include one or more infusion and/or aspiration devices 20, for example, a syringe, a bulb, a pump, or other such device. Additionally, the system 10 may include one or more monitoring and/or sensing devices 30, for example a pressure sensing device, temperature sensing device, or other like monitoring and/or sensing devices. The infusion system 10 provides for one or more selective fluid pathways for the selective delivery of one or more liquids from the liquid supply containers 16 and 18 to the catheter 25. The catheter 25 can be adapted and/or configured to deliver the fluid internally to the patient. As can be appreciated, the gas removal devices 12a–c can be put into fluid communication with one or more of the fluid pathways within the system 10 to remove gas from one or more of the liquids being delivered to the patient. It should be understood that a broad variety of suitable catheters, manifolds, liquid supply containers or reservoirs, infusion devices, monitoring and/or sensing devices and the like are generally known in the art, and may be used in such an infusion system and/or in conjunction with gas removal devices. It should also be understood that the gas removal devices and configurations disclosed herein may be used with any of a broad variety of alternative fluid delivery structures and/or systems, and are not limited for use with this type of infusion system 10 or with the particular components shown.

In the embodiment shown, the manifold 14 may include a central or main fluid delivery lumen 17 including one or more liquid supply ports 22/24. The ports 22/24 can be adapted and/or configured for selective fluid communication with the main fluid delivery lumen 17. For example, the ports 22/24 may include valves, such as stopcock type valves 32b/32c that can be individually manipulated to selectively provide fluid communication between the ports 22/24 and the main fluid delivery lumen 17. In other embodiments, other types of valves or selective flow devices may be used, for example a series of check valves or the like. Fluid containers 16/18 are in fluid communication with the ports 22/24, for example through tubing 15/19, and gas removal devices 12a/12b, respectively. By appropriate manipulation of the valves 32b/32c, fluid within the containers 16/18 can be selectively allowed to flow from the containers 16/18 through tubing 15/19, through the gas removal devices 12a/12b, and selectively through ports 22/24, respectively, and into the main fluid delivery lumen 17.

The manifold 14 may also include one or more infusion device ports 26, which can be adapted and/or configured to engage and provide fluid communication between an infusion device 20, for example, a syringe or the like, and the main fluid delivery lumen 17. Additionally, the manifold 14 may include one or more monitoring and/or sensing devices ports 27, which can be adapted and/or configured to engage and provide fluid communication between a monitoring and/or sensing device 30, for example a pressure sensing device, and the main fluid delivery lumen 17. The ports 26/27 may also optionally include valves, such as stopcock type valves or the like, that can be individually manipulated to selectively provide fluid communication between the ports 26/27 and the main fluid delivery lumen 17. For example, in this embodiment, a valve 32a is shown on port 27 to provide for selective fluid communication between the pressure sensing devices 30 and the main fluid delivery lumen 17. Such a valve could also be included on port 26 to provide for selective fluid communication between the infusion devices 20 and the main fluid delivery lumen 17.

The manifold 14 also includes a fluid outlet port 31 which can be adapted and/or configured to provide fluid communication between the main fluid delivery lumen 17 and a delivery device (such as the catheter 25), or structure engaging and in fluid communication with a delivery device. For example, in the embodiment shown, the fluid outlet port 31 is engaged and in fluid communication with a gas removal device 12c, which in turn is engaged and in fluid communication with the catheter 25.

The various components can be interconnected in appropriate fluid communication using standard connecting structures, for example permanent and/or releasable connecting structures generally known in the art. For example, in some embodiments, the gas removal devices 12a/12b can be connected to the ports 22/24 using connecting structures 28, such as quick release connecting structures, or the like. Additionally, the infusion device 20 and/or the monitoring device 30 and/or the gas removal device 12c may also be connected to the ports 26/27/31, respectively, using standard connecting structures 28, such as quick release connecting structures, or the like. Furthermore, the catheter 25 and/or the gas removal device 12c may be connected using standard connecting structures. For example, the catheter may include connecting structure 23 adapted and/or configured for engaging and providing fluid communication between the catheter and the gas removal device 12c, and such structure 23 may include a quick release type connecting structure, or the like. Additionally, any of the ports, fluid and/or device inlets or outlets, or lumen described in any of the embodiments herein may include any number of sealing devices or configurations. For example, a dual flexible membrane may be incorporated such that, if a port is not connected to another element, fluid flow out of the port is prevented. Such sealing devices or configurations may be adapted to allow various devices to be inserted therethrough while also providing a fluid seal around an inserted device.

Each of the liquid supply containers 16/18 can include one or more liquids for selective delivery to the patient. Some examples of such liquids may include drugs, marker dies, saline, flush solutions, intravenous nutrients, anesthetics, blood, and/or a broad variety of other such liquids. The liquids within the containers may be the same or different among individual containers. For example, in some embodiments, the liquid in container 18 may include a contrast media liquid, while the liquid in container 16 may include a saline or flush solution. Such a configuration may be used, for example, during a procedure wherein a contrast media is desired for delivery into a patient for diagnostic and/or visualization purposes, and saline may be used as a rinse and/or flushing agent.

The infusion system 10 can be used in a number of ways to deliver these liquids from the liquid supply containers 16/18 to the catheter 25, and ultimately to an internal location within the patient. For example, valves 32b/32c can be individually manipulated to selectively provide fluid communication between one or both of the liquid supply containers 16/18 and the main fluid delivery lumen 17. The syringe can be manipulated to draw liquid from one and/or both of the container 16/18 (depending upon valve 32b/32c orientation). The valves 32b/32c can then be manipulated to provide fluid communication between the syringe 20 and the catheter 25 through the main fluid delivery lumen 17. The syringe 20 can then be manipulated to force liquid through the main fluid delivery lumen 17 and to the catheter 25 for delivery to an internal location within the patient. Additionally, valve 32a can be individually manipulated to selectively provide fluid communication between pressure sensor 30 and the main fluid delivery lumen 17 for pressure readings at desired times during a procedure and/or during liquid delivery.

As can be appreciated, during such liquid delivery procedures, the liquid being delivered from the liquid supply containers 16/18 to the catheter 25, and ultimately to the patient, passes through at least one of the gas removal devices 12a–c for degassing. For example, liquid delivered from the fluid container 16 will pass through gas removal devices 12a and 12c. Similarly, liquid delivered from the fluid container 18 will pass through gas removal devices 12b and 12c. It should be understood that this infusion system 10 is given by way of example only, and that in many applications, each liquid being delivered to a patient may pass through more or fewer than two gas removal devices. For example, in the system shown, gas removal devices 12a and 12b could be removed from the system, and all fluid being delivered to the catheter 25 would still pass through gas removal device 12c for degassing. As another example, in the system shown, gas removal device 12c could be removed, and all liquid being delivered to the catheter 25 would still pass through either gas removal device 12a or 12b for degassing. It can also be appreciated that in some applications, only some of the liquid may need to be degassed, and therefore, a system may be set up such that some liquids being delivered may not pass through a gas removal device. However, as can be appreciated, during liquid delivery procedures, at least some of the liquid being delivered may pass through one or more gas removal devices, for example devices 12a–c, for degassing.

Figure 2:
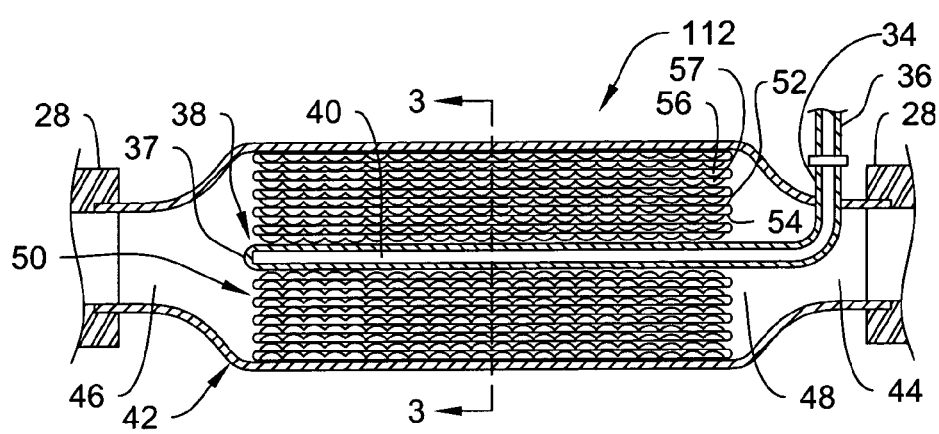
FIG. 2 is a partial cross-sectional side view of one example embodiment of a gas removal device including a filter structure including gas permeable membranes and a central arrangement of structure for gas removal.

Refer now to FIG. 2, which is a partial cross-sectional side view of one example embodiment of a gas removal device 112. For example, such a gas removal device 112 may be used as one or more of the gas removal devices 12a–c shown in the system 10 of FIG. 1, or in another gas removal system or application, as desired. The device 112 includes a housing 42 defining a liquid inlet 44, a liquid outlet 46, and a chamber 48 disposed at least partially between the inlet 44 and outlet 46. A gas filter structure 50 is disposed within the chamber 48. In the embodiment shown, the filter structure 50 includes a plurality of gas permeable membrane layers in a coiled and/or spiral configuration within the chamber, as discussed in more detail below.

Figure 4:
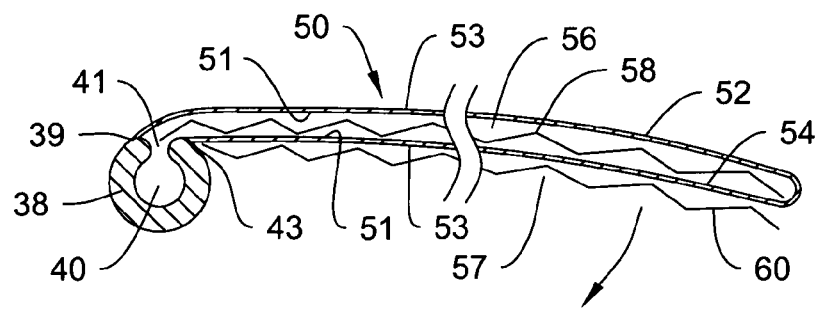
FIG. 4 is a partial cross-sectional view of the filter structure used in the example filter device of FIGS. 2 and 3, showing the filter assembly prior to rolling and insertion into a filter housing.

As seen best in FIG. 4, which is a partial cross-sectional side view showing the filter structure 50 absent the housing and in an expanded and/or uncoiled form, the filter structure 50 includes a first gas permeable membrane layer 52 and a second gas permeable membrane layer 54. The first and second layers 52/54 form a gas collection space 56 disposed between the two layers 52/54. The layers 52/54 each include an inner surface 51 and an outer surface 53. The inner surfaces 51 at least partially define the bounds of the gas collection space 56, and the outer surfaces 53 at least partially define a contact area, and/or liquid flow space 57 for liquid passing within the device 112. When the filter structure 50 is placed into a housing 42, the outer surfaces 53, potentially in combination with the inner surface of the housing 42, will help define the liquid flow space 57. The outer surfaces 53 (i.e., liquid contact area and/or liquid flow space 57) are separated from the gas collection space 56 by at least one of the membrane layers 52/54. Therefore, as liquid passes through the liquid flow space and over the outer surfaces 53 of the gas permeable membrane layers 52/54, gas (if any) within the liquid can permeate one of the gas permeable membrane layers 52/54 and enter into the gas collection space 56. Some examples of materials and structures that may be used for the gas permeable membrane layers 52/54 will be discussed in more detail below.

In the embodiment shown, the filter structure 50 can also include one or more spacer layers 58 (i.e., permeate spacer layer) disposed within the gas collection space 56. The spacer layer 58 can aid in maintaining the gas collection space 56 open by keeping the inner surfaces 51 of the two membrane layers 52/54 separate, while still allowing for the flow of gas within the gas collection space 56. Additionally, the filter structure 50 can also include one or more spacer layers 60 (i.e., flow spacer layer) disposed within the liquid flow space 57, for example, along the outer surfaces 53 of one or both of the membrane layers 52/54. The spacer layer 60 can aid in maintaining the liquid flow space 57 open by keeping the outer surfaces 53 of the two membrane layers 52/54 separate from each other and/or appropriately spaced from other structures, such as the housing or gas venting structure, while still allowing for the flow of liquid within the liquid flow space 57. Some examples of materials and structures that may be used for the spacer layers 58 and 60 will be discussed in more detail below.

Figure 5:
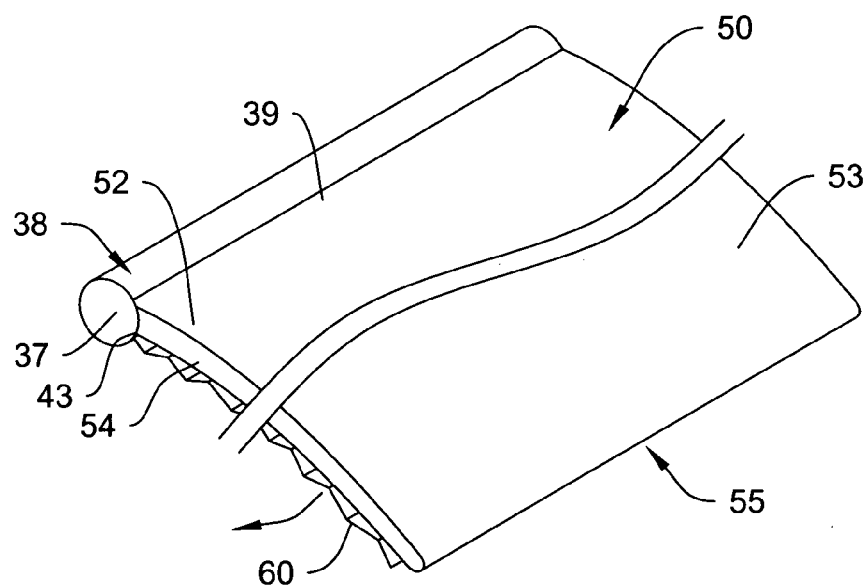
FIG. 5 is a partial perspective view of the filter structure used in the example filter device of FIGS. 2 and 3, showing the filter structure absent the housing and in an un-rolled configuration.

Referring to FIG. 5, in the embodiment shown, the layers 52/54 are in the form of generally flat sheets or leafs of material having outer peripheries 55 that are generally overlapping with one another. The layers 52/54 can be connected to each other about at least a substantial portion of their outer periphery to define the gas collection space 56. For example, in the embodiment shown, the layers 52/54 include an outer periphery 55 that is generally rectangular in shape, and the layers 52/54 can be attached to each other about the outer periphery of this rectangular shape to define the gas collection space 56. It should be understood, however, that in other embodiments, the layers 52/54 may include an outer periphery 55 that is of a different shape, for example, circular, oval, square, triangular, or other multi-sided geometries, as desired, or the like. The layers 52/54 can be connected using any of a broad variety of suitable attachment techniques and/or materials, for example, adhesive bonding, heat bonding, welding, soldering, mechanical bonding, friction bonding, crimping, the use of additional attachment and/or connecting structures, or the like. Those of skill in the art will recognize that the particular attachment techniques and/or materials used will depend at least somewhat on the properties of the material being bonded and/or upon the desired characteristics of the attachment.

Referring back to FIG. 2, the gas collection space 56 is in fluid communication with a gas outlet 34 that extends through the housing 42. In the embodiment shown, fluid communication between the gas collection space 56 the gas outlet 34 is provided by a conduit 38 extending within the housing, the conduit 38 connecting and in fluid communication with the gas collection space 56 the gas outlet 34. In the embodiment shown, the conduit 38 is a hollow tubular member having a wall defining a lumen 40 therein that provides fluid communication between the gas collection space 56 and the gas outlet 34. There is no fluid communication between the chamber 48 and the lumen 40, and in that regard, the end 37 of the tubular member 38 opposite the gas outlet 34 may be closed and/or blocked to prevent such fluid communication.

Figure 3:
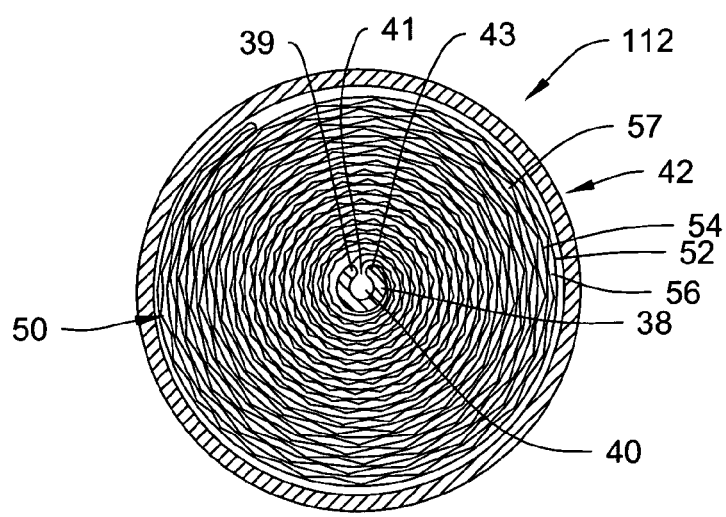
FIG. 3 is a partial cross-sectional view taken along a vertical line perpendicular to a longitudinal axis of the gas removal devices of FIG. 2 (i.e., along line 3—3 of FIG. 2)

Referring to FIGS. 3 and 4, one or more opening 41 is defined in the wall of the tubular member 38 to expose the lumen 40 therein and being adapted to provide for fluid communication between the gas collection space 56 and the lumen 40. In the embodiment shown, fluid communication between the gas collection space 56 and the lumen 40 through the opening 41 is provided by attaching the gas permeable membrane layers 52/54 to the tubular member 38 in such a manner as to allow for such fluid communication. For example, the first layer 52 may be attached to the tubular member 38 along a first side of the opening 41, for example at attachment point 39, and the second layer 54 may be attached to the tubular member 38 along a second side of the opening 41, for example at attachment point 43. This arrangement thereby provides for fluid communication between the gas collection space 56 and the lumen 40, and ultimately, provides for fluid communication between the gas collection space 56 and the gas outlet 34.

As seen in FIGS. 2 and 3, the gas filter structure 50 is disposed within the chamber 48 in a manner such that the membrane layers 52/54 are in a coiled and/or spiral configuration within the chamber 48. In the embodiment shown, the membrane layers 52/54 are coiled about a longitudinal axis of the housing 42, and in particular, are coiled about a longitudinal axis of the tubular member 38. For example, after attachment of the membrane layers 52/54 to the tubular member 38, as shown in FIGS. 4 and 5, the membrane structure may be coiled and/or rolled and/or otherwise manipulated around the tubular member 38, for example as shown by the arrows in FIGS. 4 and 5. Referring back to FIGS. 2 and 3, such coiling of the membrane layers 52/54 results in multiple levels and/or stages and/or layers of the membrane layers 52/54. Likewise, because the membrane layers 52/54 at least partially define the gas collection space 56 and the liquid flow space 57, multiple levels and/or stages and/or layers of the gas collection space 56 and the liquid flow space 57 are also created. This type of coiled and/or spiral configuration may allow for a filter structure 50 to have a sufficient amount of surface area for contact with liquid flowing through the device, while reducing the amount of space required by the filter structure 50. In at least some embodiments, the filter structure 50 may fill substantially the entire cross sectional area of at least a portion of the chamber 48. Such an arrangement may allow for the efficient use of space, and also may be adapted to facilitate contact between the liquid being degassed and at least a portion of the filter structure 50 (i.e., the liquid cannot pass through the device without passing through at least a portion of the filter structure.).

It should be understood that while the housing is shown as a generally elongated structure having a generally circular cross section, in other embodiments, the housing may take other forms or shapes. However, in at least some embodiments, the generally circular cross section can provide certain advantages. For example, in embodiments including a coiled and/or spiraled filter structure configuration, the circular cross section of the housing may allow for the generally circular coiled and/or spiraled filter structure to fill substantially the entire cross sectional area of the housing. However, it will be understood that the filter structure may take other shapes and/or forms, and therefore, the shape of the housing may be adapted to accommodate these other shapes and/or forms.

Additionally, in some embodiments, the size of the gas collection space 56 and/or the liquid flow space 57 may also be controlled to facilitate removal of gasses from the liquid. It should also be recognized that the length and width of the membrane layers 52/54 also at least partially aid in defining the size parameters of the gas collection space 56 and/or the liquid flow space 57. The thickness and porosity of the membrane layers 52/54, acceptable flow rates of fluids within the gas collection space 56 and/or the liquid flow space 57, and the desired level of degassing may also be taken into consideration when determining appropriate size parameters.

For example, in some embodiments, the size of the liquid flow space 57 can be configured to provide for acceptable contact between the liquid and the outer surface of the membranes 52/54 for degassing, while also allowing for an acceptable flow rate of the liquid through the liquid flow space 57. Depending upon the particular layers used, and upon the desired performance of the device, those of skill in the art will be able to determine appropriate sizing for the liquid flow space 57. In the embodiment shown, the spacer layer 60 may at least partially aid in defining the size of the liquid flow space 57. In some example embodiments, the liquid flow space 57 can have a thickness (gap) in the range of about 20 or more microns, or in the range of about 40 to about 1000 microns. In some embodiments, the length of the liquid flow space 57 is at least partially defined by the width of the membrane layers 52/54, or in other words the distance of the filter material along the longitudinal axis of the device. In some embodiments, the liquid flow space 57 may have a length in the range of about 0.1 inches, or more, or in the range of about 0.2 to about 20 inches or more, or in the range of about 0.5 to about 15 inches or more. In some embodiments, the width of the liquid flow space 57 is at least partially defined by the length of the membrane layers 52/54, or in other words the distance of the membrane material, for example, measured as it spirals about the longitudinal axis of the device. In some embodiments, the liquid flow space 57 may have a width in the range of about 0.5 inches, or more, or in the range of about 0.5 to about 50 inches or more, or in the range of about 0.5 to about 30 inches or more.

Likewise, in some embodiments, the size of the gas collection space 56 can be configured to provide for an acceptable flow rate of the gas through the gas flow space 56, while maintaining an efficient use of space. Depending upon the particular layers used, and upon the desired performance of the device, those of skill in the art will be able to determine appropriate sizing for the gas collection space 56. In the embodiment shown, the spacer layer 58 may at least partially aid in defining the size of the gas collection space 56. In some example embodiments, the gas collection space 56 can have a thickness (gap) in the range of about 20 or more microns, or in the range of about 40 to about 1000 microns. In some embodiments, the length of the gas collection space 56 is at least partially defined by the width of the membrane layers 52/54, or in other words the distance of the filter material along the longitudinal axis of the device. In some embodiments, the gas collection space 56 may have a length in the range of about 0.1 inches, or more, or in the range of about 0.2 to about 20 inches or more, or in the range of about 0.5 to about 15 inches or more. In some embodiments, the width of the gas collection space 56 is at least partially defined by the length of the membrane layers 52/54, or in other words the distance of the membrane material, for example, measured as it spirals about the longitudinal axis of the device. In some embodiments, the gas collection space 56 may have a width in the range of about 0.5 inches, or more, or in the range of about 0.5 to about 50 inches or more, or in the range of about 0.5 to about 30 inches or more.

In some embodiments, the removal of dissolved gasses present in the liquid can be additionally facilitated by use of negative pressure and/or vacuum applied to the gas collection space 56. For example, vacuum pressure may be applied to the gas outlet 34 which is in fluid communication with the gas collection space 56. For example, a vacuum line 36 extending from a vacuum creating device and/or apparatus (not shown) may be attached to the gas outlet 34 for the application of negative pressure. Any of a broad variety of vacuum creating devices and/or apparatuses generally know in the art may be used, for example, a pump, syringe, bulb, or the like. Such vacuum may facilitate removal of dissolved gasses from the liquid according to Henry's Law.

The material used for the gas permeable membrane layers 52/54 may include any of a broad variety of generally gas permeable material. For example, the membrane layer material can be a microporous hydrophobic membrane, such as are available commercially as polyolefin membranes. Example materials include: polypropylene, polyethylene, or polymethylpentene. In some embodiments, the membrane layer material can include a wall thickness in the range of about 10 to about 300 microns, or in some embodiments in the range of about 25 to about 210 microns, or in some embodiments in the range of about 60 to about 175 microns. In some embodiments, the membrane layer material can include a pore size in the range of about 0.01 to about 0.2 microns, which in some such embodiments may be sufficiently small to prevent substantial liquid breakthrough. In some embodiments, the membrane layer material can include a porosity in the range of about 10 to about 50%, which in some such embodiments may be sufficiently high to provide adequate flux of gas and gas bubble passage from the liquid contact area, which is at least partially defined by outer surfaces 53, and the gas collection space 56, which is disposed between the two layers 52/54. In some embodiments, the membrane layers 52/54 are constructed of suitable FDA grade materials. A porous hydrophobic membrane can allow for the direct removal of bubbles from liquid, such as aqueous fluids, without substantial liquid penetration into the pores according to the Young-Laplace formula.

Although microporous hydrophobic membranes are described above, any porous material, whether hydrophobic or hydrophilic, can be used to form the layers 52/54, with the application of a thin coating or skin of a polymer having suitable permeability to the dissolved gasses (for example, oxygen, nitrogen, carbon dioxide) in the liquid passed adjacent the liquid contact area, but rendering the pores of the layers 52/54 impermeable to passage of the liquid there through. Example polymer coatings include silicones, polymethylpentene, and other polymers, some of which may be FDA grade. The polymer skin is preferably applied to the liquid contact surface (the outer surfaces 53) of the layers 52/54, to prevent liquid penetration into the pores. In some embodiments, although the polymer skin may prevent direct removal of bubbles present in the liquid, entrained bubbles in the liquid will dissolve into the liquid once sufficient dissolved gasses are removed from the liquid. Once dissolved, the gasses can be removed from the liquid. Such porous material, when provided with such a coating or skin, can also be considered a gas permeable membrane layer.

The material used for the spacer layers 58/60 may include any of a broad variety of material generally suitable for the intended purpose of these layers. For example, in some embodiments, the material used for spacer layers 58 can be sufficiently sized and firm to maintain the gas collection space 56 open at a desired size, while still allowing for the flow of gas within the gas collection space 56. Additionally, in some embodiments, the material used for spacer layer 60 can be sufficiently sized and firm to maintain the liquid flow space 57 open at a desired size, while still allowing for the flow of liquid within the liquid flow space 57 at a sufficient level. In some embodiments, the material used for one and/or both spacer layers 58/60 can include material in the form of a weave, a mesh, a screen, a knit, or other porous structure that allows for the desired degree of gas and/or liquid porosity, respectively. Some example materials include such structures made out of natural fibers, polymers, metals, metal alloys, or the like. Some examples of suitable fabrics having a thickness in the range 20 microns or more, or in the range of about 40 to about 1,000 microns, have a pore size in the range of about 1–800, have a void fraction in the range of about 0.3 to about 0.8, or in some embodiments, in the range of about 0.4 to about 0.7, and may be made, for example, from polymers such as polyester, nylon, polypropylene, fluorocarbon, PEEK, or combinations thereof, or other material.

The housing can be made of any suitable material to house the filter structure 50, for example a broad variety of polymers, metals, or metal alloys could be used. Some examples of suitable polymer materials include polycarbonate materials, and the like.

Figure 6:
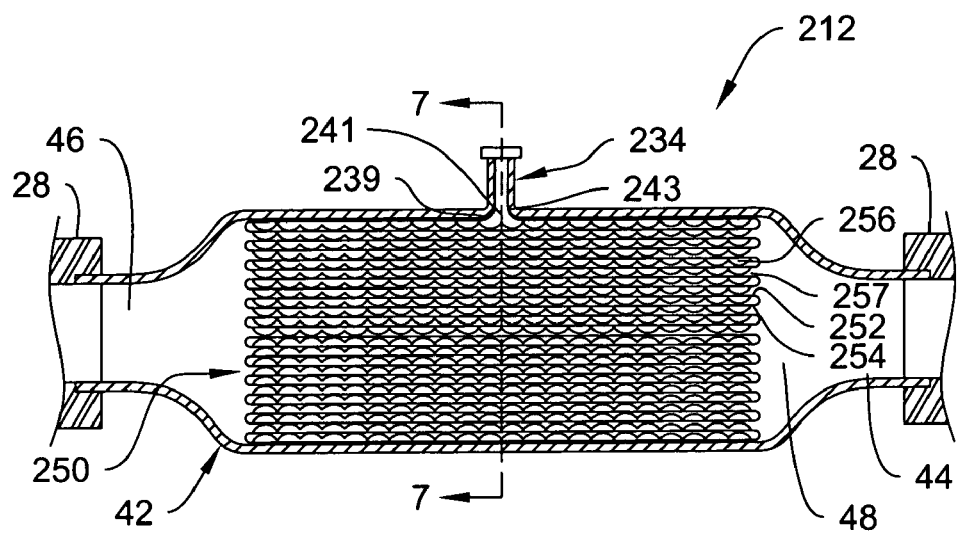
FIG. 6 is a partial cross-sectional side view of one example embodiment of a gas removal device including a side arrangement of structure for gas removal.
Figure 7:
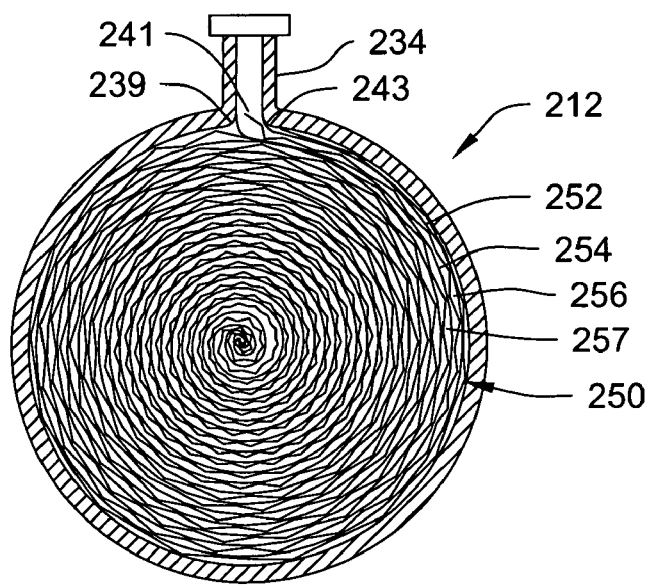
FIG. 7 is a partial cross-sectional view of the gas removal devices of FIG. 6 taken along line 7—7 of FIG. 6.
Figure 8:
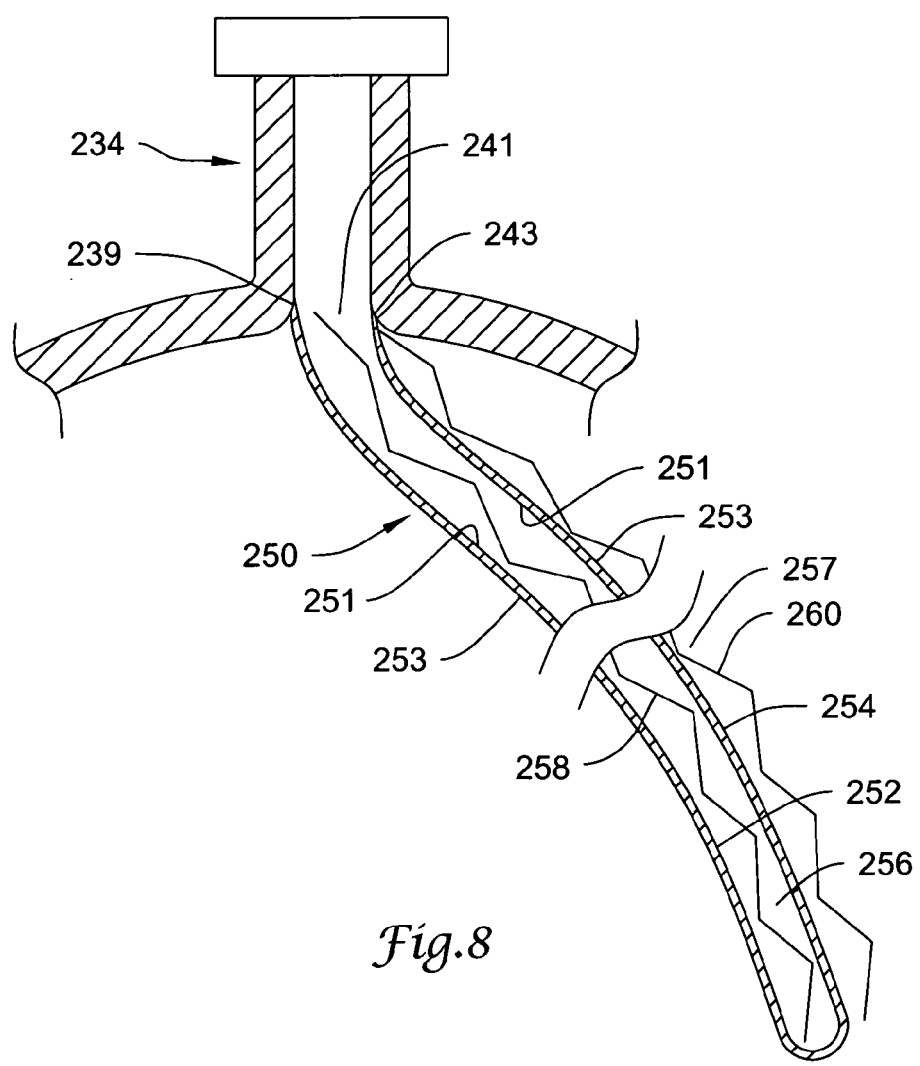
FIG. 8 is a partial cross-sectional view of the filter structure used in the example filter device of FIGS. 6 and 7, showing the filter structure shown in an unrolled configuration and in communication with a side port.

Refer now to FIGS. 6–8 for discussion of another example embodiment of a gas removal device 212 that is somewhat similar to the device 112 shown above, wherein like reference numbers indicate similar structure. The device 212 includes a gas filter structure 250 disposed within the chamber 48 of the housing 42. The gas filter structure 250, similar to structure 50 discussed above, includes a plurality of gas permeable membrane layers in a coiled and/or spiral configuration within the chamber 48. For example, the filter structure 250 includes a first gas permeable membrane layer 252 and a second gas permeable membrane layer 254 defining a gas collection space 256 disposed between the two layers 252/254. The layers 252/254 each include an inner surface 251 and an outer surface 253, and the inner surfaces 251 at least partially define the bounds of the gas collection space 256, and the outer surfaces 253 at least partially define a contact area, and/or liquid flow space 257 for liquid passing within the device 212. When the filter structure 250 is placed into a housing 42, the outer surfaces 253, potentially in combination with the inner surface of the housing 42, will help define the liquid flow space 257. The outer surfaces 253 (i.e., liquid contact area and/or liquid flow space 257) are separated from the gas collection space 256 by at least one of the membrane layers 252/254. Therefore, as liquid passes through the liquid flow space and over the outer surfaces 253 of the gas permeable membrane layers 252/254, gas (if any) within the liquid can permeate one of the gas permeable membrane layers 252/254 and enter into the gas collection space 256. Additionally, the filter structure 250 can also include one or more spacer layers 258 (i.e. permeate spacer layer) as seen in FIG. 8 disposed within the gas collection space 256, and one or more spacer layers 260 (i.e., flow spacer layer) as seen in FIG. 8 disposed within the liquid flow space 257, for example, along the outer surfaces 253 of one or both of the membrane layers 252/254.

So, as can be seen, in many regards, the gas filter structure 250 can include substantially the same structure, form and materials as discussed above regarding filter structure 50. However, in this embodiment, the gas collection space 256 is placed in fluid communication with a gas outlet 234 using a different construction. In this embodiment, the gas outlet 234 defines one or more openings 241 in the wall of the housing 42. In the embodiment shown, fluid communication between the gas collection space 256 and the gas outlet 234 is provided through the opening 241 by attaching the gas permeable membrane layers 252/254 to the housing 42 in such a manner as to allow for such fluid communication. For example, the first layer 252 may be attached to the housing 42 along a first side of the opening 241, for example at attachment point 239, and the second layer 254 may be attached to the housing 42 along a second side of the opening 241, for example at attachment point 243. This arrangement thereby provides for fluid communication between the gas collection space 256 and the gas outlet 234.

Figure 9:
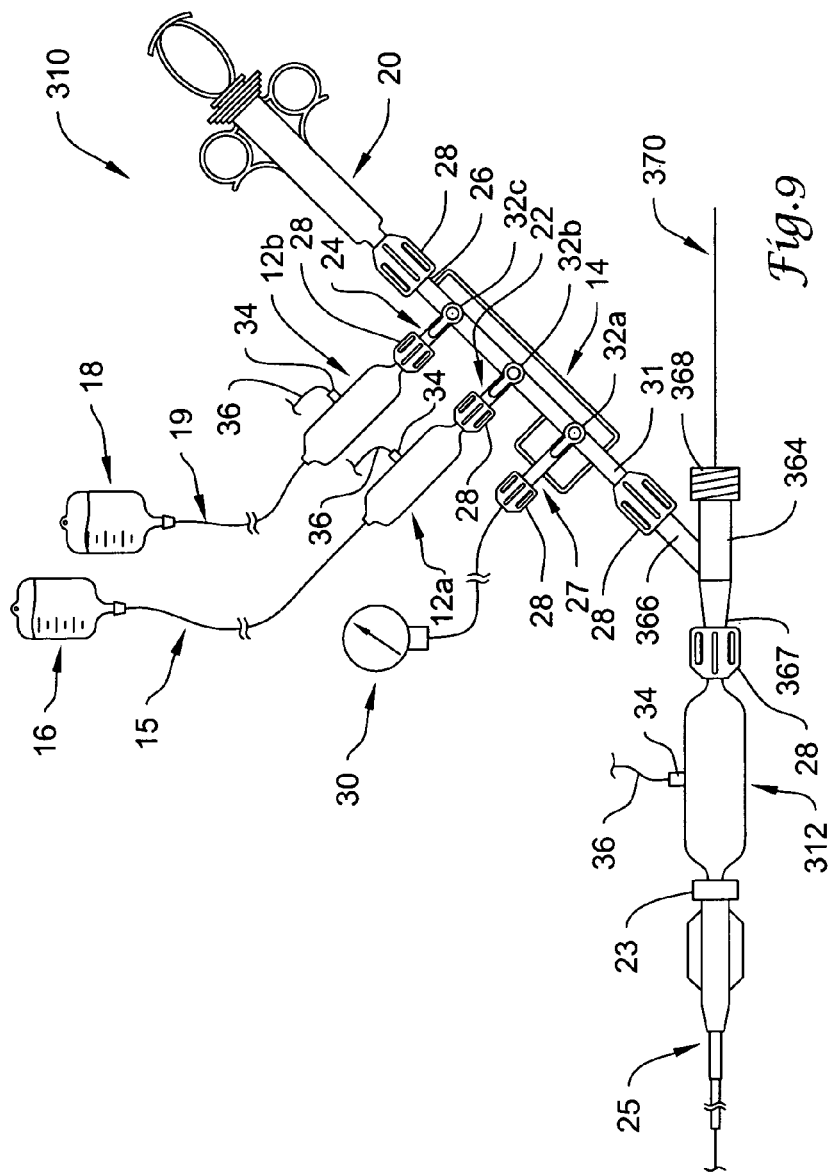

Refer now to FIG. 9, which is a side view of another example embodiment of a liquid delivery system 310. The system 310 includes some similar structure as the system 10 described above with reference to FIG. 1, wherein like reference numbers indicate similar structure. For example, the catheter 25, manifold 14, liquid supply containers 16/18, gas removal devices 12a/12b, and associated structure can be generally the same as those described above.

However, the system 310 of FIG. 9 includes a wye adapter 364 and an alternative configuration for a gas removal device 312. The wye adapter 364 and the gas removal device 312 are configured to allow fluid communication between the manifold 14 and the catheter 25 while also allowing for the insertion of an elongated medical device 370, such as a guidewire, catheter, of the like, into the system 310, and ultimately into and/or through the catheter 25.

The wye adapter 364 can include a medical device inlet port 368 adapted and/or configured for the introduction of a medical device, such as a guidewire 370. The wye adapter 364 also includes a fluid inlet port 366 configured for connection and fluid flow communication with the manifold 14, for example using connection structure 28, and a fluid outlet/device outlet port 367 configured for connection and fluid flow communication with the gas removal device 312.

The wye adapter 364 can include one or more lumens extending from the medical device inlet port 368 to the outlet port 367 for passage of the medical device, and may also include one or more lumens extending from the fluid inlet port 366 to the outlet port 367 for passage of the fluid from the manifold 14 to the gas removal device 312. Suitable configurations for such a wye adapter 364 are generally known in the art.

Figure 10:
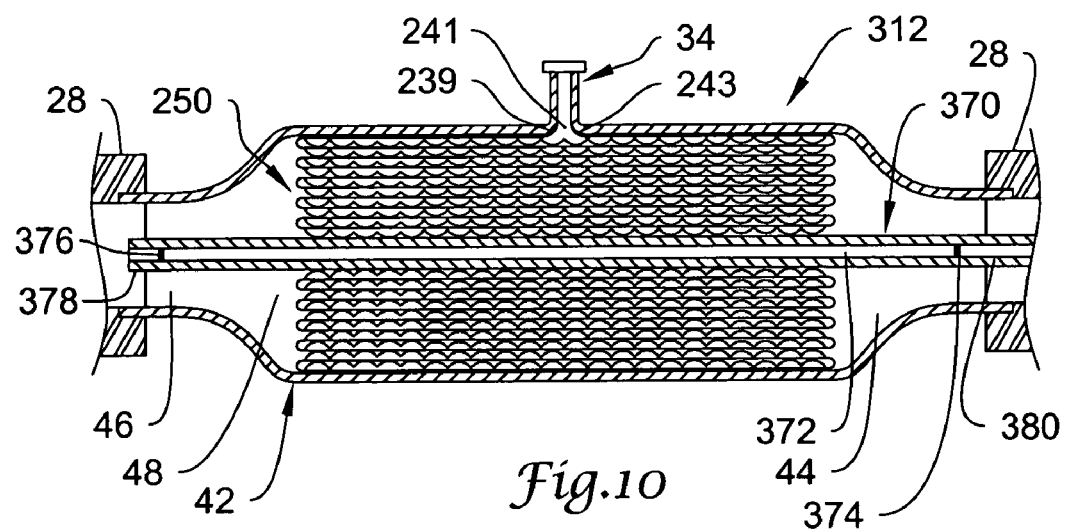
FIG. 10 is a partial cross-sectional side view of one example embodiment of a gas removal device including a side venting configuration and including a device lumen.

It should also be appreciated that in this system 310, the gas removal device 312 must also include structure allowing the insertion and/or passage of the medical device 370 there through. In that regard, reference is now made to FIG. 10, which shows another example embodiment of a gas removal device 312. The device 312 is substantially similar to the embodiment shown in FIGS. 6–8, and as discussed above, wherein like reference numerals indicate similar structure. For example, the filter structure 250 and arrangement is substantially similar to the embodiment shown in FIGS. 6–8. However, in this embodiment, the device 312 further includes a conduit 370 extending through at least a portion of the chamber 48 within the housing 42. The conduit 370 extends from adjacent the liquid inlet 44 to adjacent the liquid outlet 46, and is configured and/or adapted to receive an elongated medical device, for example 370 in FIG. 9. In the embodiment shown in FIG. 10, the conduit 370 is a tubular member defining a lumen 372 configured and/or sized for receiving or passing an elongated medical device there through. The proximal end 380 of the tubular member 370 is coaxially disclosed adjacent the fluid inlet port 44, and the distal end 378 is coaxially disposed adjacent the outlet port 46, although this is not necessary in all embodiments. Additionally, conduit 370 may include one or more sealing devices or configurations that may seal the lumen 372 such that fluid flow, for example in a direction away from the distal end 378, is reduced and/or prevented. Such a sealing device may be adapted to allow various devices to be inserted there through while also providing a fluid seal around an inserted device. For example, a dual flexible membrane may be incorporated such that, fluid flow out of the proximal end 380 of the lumen 372 is prevented. The embodiment shown indicates one or more sealing structures 374/376 that are disposed within the lumen 372 of the conduit 370.

Figure 11:
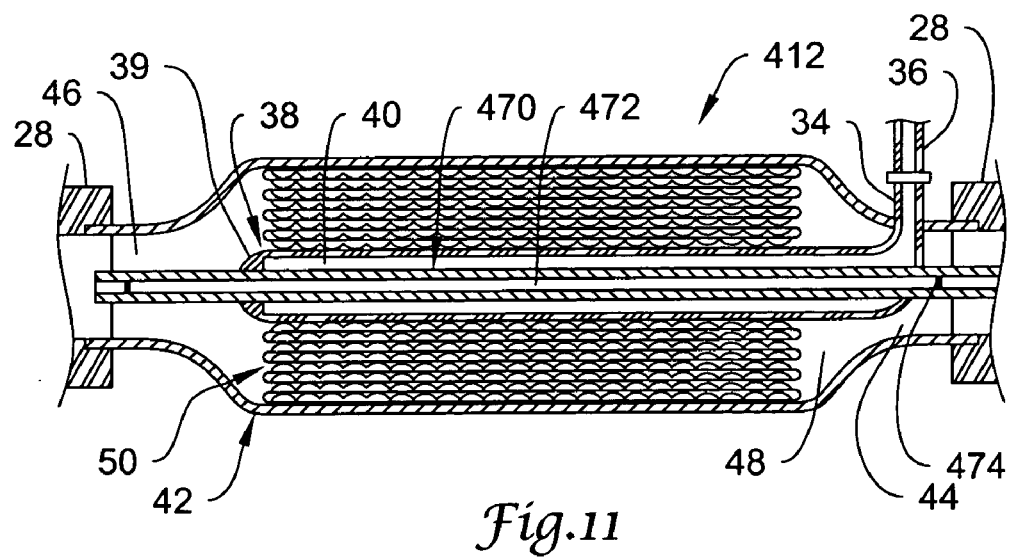
FIG. 11 is a partial cross-sectional side view of one example embodiment of a gas removal device including a central venting configuration and including a device lumen.

FIG. 11 shows another alternative embodiment of a gas removal device 412 that may be used, for example, in place of the gas removal device 312 of the liquid delivery system 310 shown in FIG. 9. The device 412 is substantially similar to the device 112 shown in FIGS. 2–5, and as discussed above, wherein like reference numerals indicate similar structure. For example, the filter structure 50 and arrangement is substantially similar to the embodiment shown in FIGS. 2–5. However, in this embodiment, the device 412 also includes a conduit 470 extending through at least a portion of the chamber 48 within the housing 42, for example, as described above with reference to the device 312 shown in FIG. 10. The conduit 470 extends from adjacent the liquid inlet 44 to adjacent the liquid outlet 46, and is configured to receive an elongated medical device. In the embodiment shown, the conduit 470 is a tubular member defining a lumen 472 configured for receiving and/or passing an elongated medical device there through. In the embodiment shown, the gas conduit 38 and the medical device conduit 470 can be coaxially disposed along at least a portion of the lengths thereof, however, this is not required.

Figure 12:
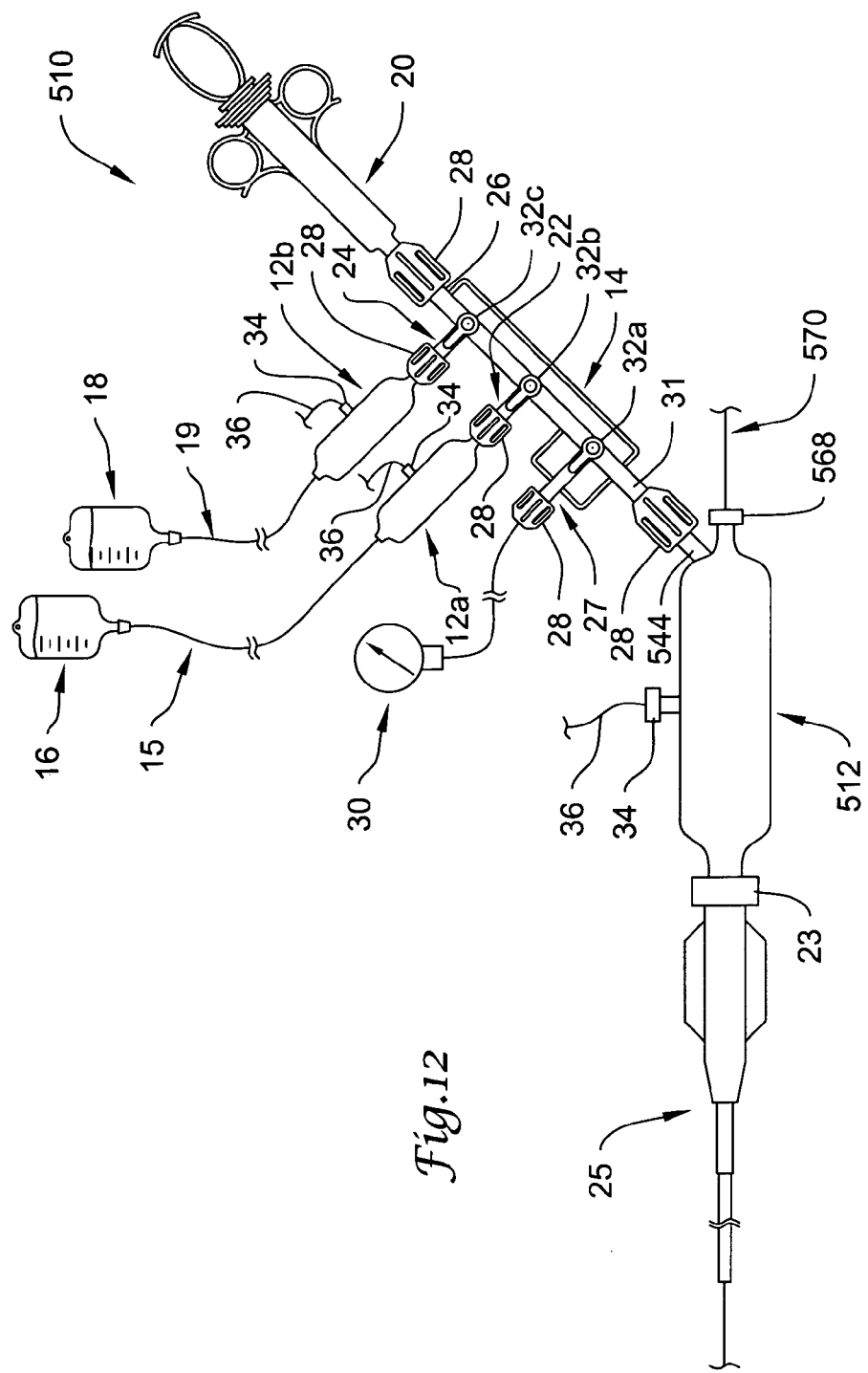
FIG. 12 is a side view of another example embodiment of a catheter infusion system including a plurality of gas removal devices, wherein one of the gas removal devices includes structure for connection to a fluid delivery system, such as a manifold, and structure for allowing insertion of a device into and through the gas removal device separate from the manifold.

FIG. 12 is side view of another example embodiment of a liquid delivery system 510. The system 510 includes some similar structure as the systems 10 and 310 described above with reference to FIGS. 1 and 9, wherein like reference numbers indicate similar structure. For example, the catheter 25, manifold 14, liquid supply containers 16/18, gas removal devices 12a/12b, and the other structure associated therewith can be generally the same as those described above. Additionally, similar to the embodiment shown in FIG. 9, the system 510 includes structure allowing for the insertion of an elongated medical device 570, such as a guidewire, catheter, of the like, into the system 510, and ultimately to the catheter 25. However, in this embodiment, the system 510 does not include a wye adapter (Y-adapter), but rather includes an alternative embodiment of a gas removal device 512 that includes structure allowing for direct fluid communication with the manifold 14 and for the direct insertion of an elongated medical device 570. In this embodiment, the housing of the device 512 defines a medical device port 568 adapted and/or configured for the introduction of a medical device 570 and a separate fluid inlet port 544 configured for connection and fluid flow communication with the manifold 14, for example using connection structure 28.

Figure 13:
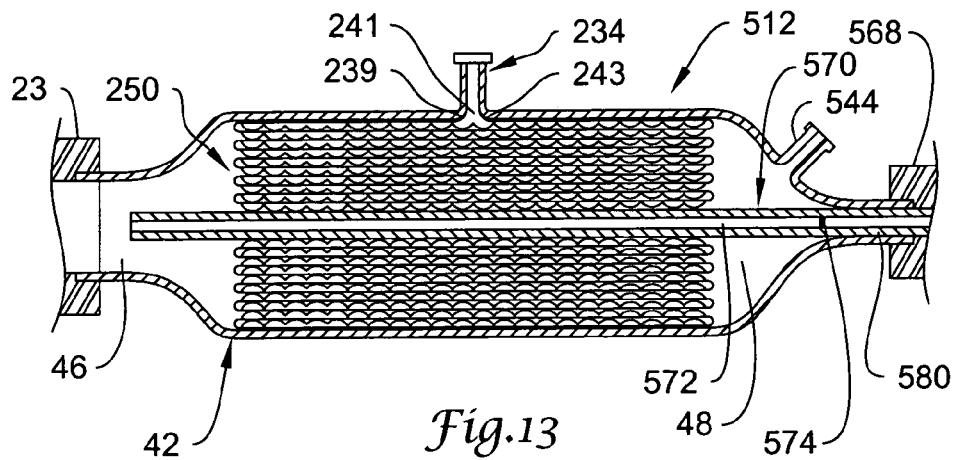
FIG. 13 is a partial cross-sectional side view of one example embodiment of a gas removal device including structure for connection to a fluid delivery system and structure for allowing insertion of a device into and through the gas removal device, as in FIG. 12, wherein the gas removal device includes a side venting configuration and a device lumen.

For example, reference is now made to FIG. 13, which shows a cross sectional view of one example embodiment of such a gas removal device 512. The device is substantially similar to the structure of the device 312 shown in FIG. 10, wherein similar reference numbers indicate similar structure. For example, the filter structure 250 and arrangement is substantially similar to the embodiment shown in FIG. 10 (which is substantially the same filter structure 250 of FIGS. 6–8). Additionally, the device 512 also includes a medical device conduit 570 including a lumen 572 extending through at least a portion of the chamber 48 within the housing 42, which is substantially similar in form and function to the conduit 370 including lumen 372 of FIG. 10. For example, the conduit 570 can be a tubular member configured to receive an elongated medical device.

However, in this embodiment, the device 512 includes a separate medical device port 568 and fluid inlet port 544, as discussed above. Therefore, the proximal end 580 of the tubular member 570 is not coaxially disposed within the fluid inlet port 544, but rather, the fluid inlet port 544 is spaced from the tool inlet port 568. In this embodiment, the tool inlet port 568 is disposed generally along the longitudinal axis of the device 512, while the fluid inlet port 544 is oriented at an angle with the longitudinal axis of the device 512. Additionally, one or more sealing structures 574 can be disposed within the lumen 572 of the conduit 570, such as the sealing structures described above with reference to FIG. 10.

Figure 14:
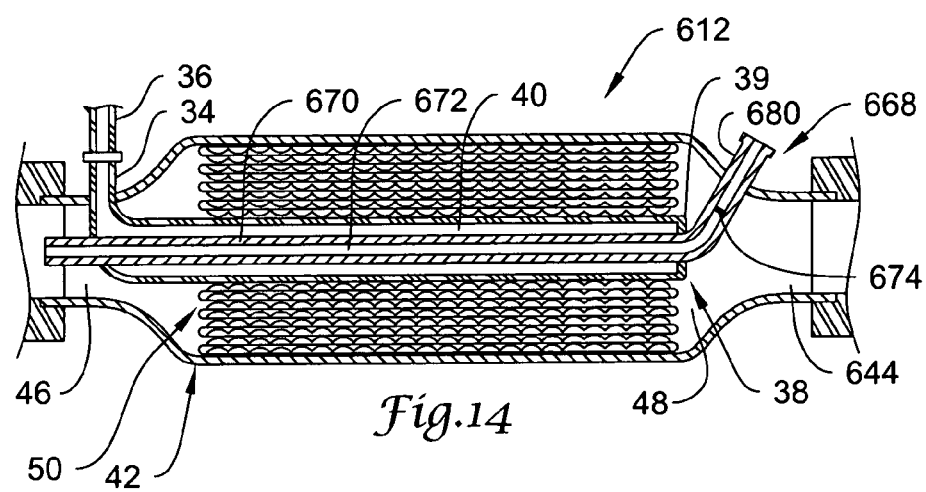
FIG. 14 is a partial cross-sectional side view of one example embodiment of a gas removal device including structure for connection to a fluid delivery system and structure for allowing insertion of a device into and through the gas removal device, similar to that shown in FIG. 13, but wherein the gas removal device includes a central venting configuration and the device lumen extends through a side wall of the device housing.

FIG. 14 shows another alternative embodiment of a gas removal device 612 that may be used, for example, in place of the gas removal device 512 of a liquid delivery system 510 shown in FIG. 12. The device 612 is substantially similar to the embodiment shown in FIG. 11, and as discussed above, wherein like reference numerals indicate similar structure. For example, the filter structure 50 and arrangement is substantially similar to the embodiment shown in FIG. 11 (which is substantially the same filter structure 50 of FIGS. 2–5). Additionally, the device 612 also includes a medical device conduit 670 including a lumen 672 extending through at least a portion of the chamber 48 within the housing 42, which is substantially similar in form and function to the conduit 470 including lumen 472 of FIG. 11. For example, the conduit 670 can be a tubular member configured to receive an elongated medical device. In the embodiment shown, the gas conduit 38 and the medical device conduit 670 can be coaxially disposed along at least a portion of the lengths thereof, however, this is not required.

However, in this embodiment, the device 612 includes a separate medical device port 668 and fluid inlet port 644, for example, as discussed above with reference to FIGS. 12 and 13. Therefore, the proximal end 680 of the tubular member 670 is not coaxially disposed within the fluid inlet port 644, but rather, the fluid inlet port 644 is spaced from the tool inlet port 668. In this embodiment, the fluid inlet port 644 is disposed generally along the longitudinal axis of the device 612, while the tool inlet port 668 is oriented at an angle with the longitudinal axis of the device 612. Additionally, one or more sealing structures 674 can be disposed within the lumen 672 of the conduit 670, such as the sealing structures described above with reference to FIG. 10.

Figure 15:
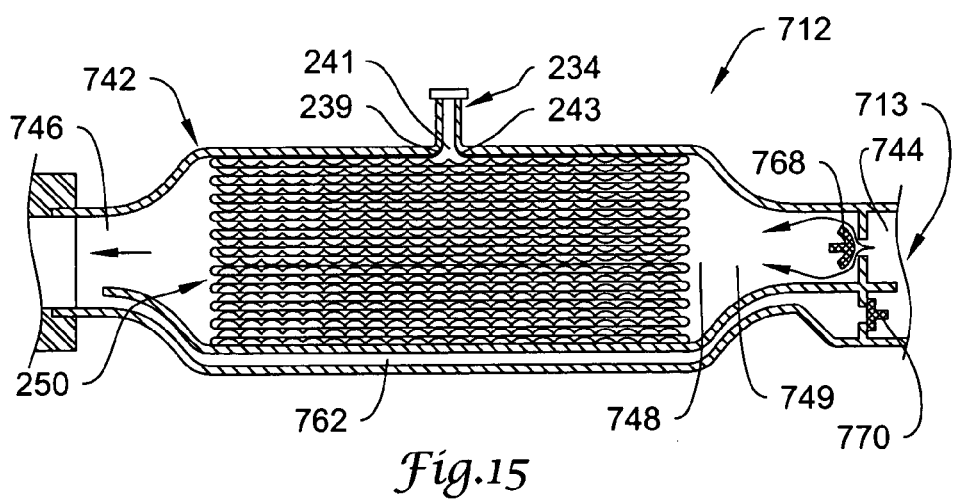
FIG. 15 is a partial cross-sectional side view of another example embodiment of a gas removal device similar to the one shown in FIG. 7, but including a flow return system, wherein in the embodiment shown, a check valve system is shown.
Figure 16:
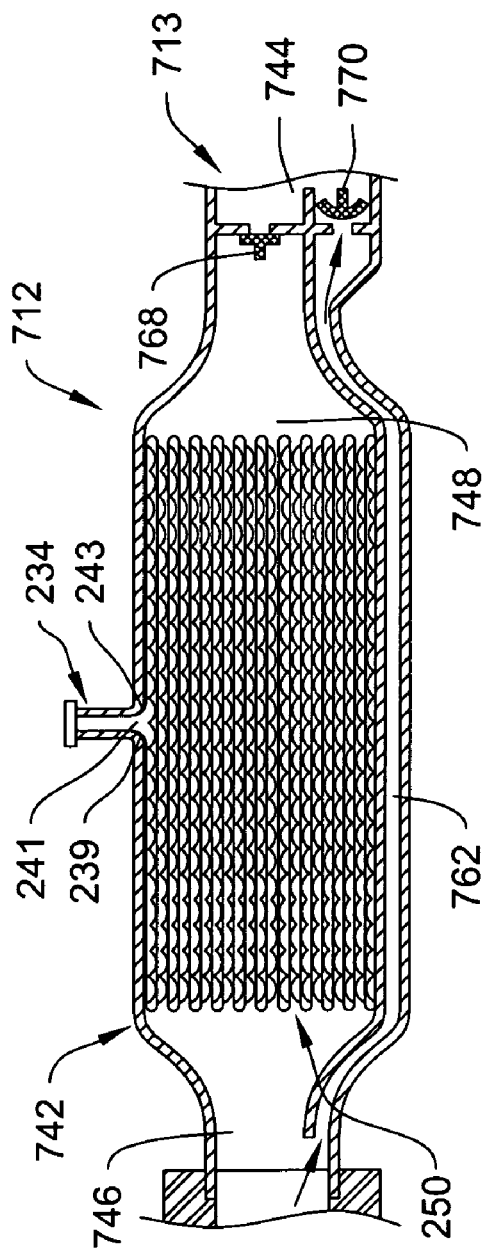
FIG. 16 is a partial cross-sectional side view of the gas removal device of FIG. 15, showing check valve system preventing flow into the filter and providing a reverse flow of fluid around the filter.

FIGS. 15 and 16 disclose another alternative embodiment of a gas removal device 712. In some regards, the device 712 is substantially similar to the structure of the device shown in FIGS. 6–8, wherein similar reference numbers indicate similar structure. For example, the filter structure 250 and arrangement is substantially similar to the embodiment shown in FIGS. 6–8.

However, in this embodiment, the device 712 also includes structure that may allow for the reverse flow of liquid through the device 712 such that the liquid flowing in the reverse direction does not flow through the filter structure 250. In this embodiment, the housing 742 includes a chamber 748 that includes a first liquid path conduit 749 in fluid communication with the liquid inlet 744 and the liquid outlet 746, and a second liquid path conduit 762 in fluid communication with the liquid inlet 744 and the liquid outlet 746. The device 712 also includes a valve assembly 713 adapted and/or configured to allow for the flow of liquid from the liquid inlet 744 to the liquid outlet 746 through the first liquid path conduit 749 while preventing the flow of liquid from the liquid inlet 744 to the liquid outlet 746 through the second liquid path conduit 762. The valve assembly 713 is further configured to allow for the flow of liquid from the liquid outlet 746 to the liquid inlet 744 through the second liquid path conduit 762 while preventing the flow of liquid from the liquid outlet 746 to the liquid inlet 744 through the first liquid path conduit 749.

In the embodiment shown, the valve assembly 713 includes a first one way check valve 768 disposed within the first liquid path conduit 749 configured to allow one-directional liquid flow from the liquid inlet 744 to the liquid outlet 746 through the first liquid path conduit 749. The valve assembly 713 also includes a second one way check valve 770 disposed within the second liquid path conduit 762 configured to allow one-directional liquid flow from the liquid outlet 746 to the liquid inlet 744 through the second liquid path conduit 762. FIG. 15 shows fluid flow through the first liquid path—through the filter structure 250. FIG. 16 shows fluid flow through the second liquid path 762—away from, and not through the filter structure 250. It should be understood that such valve assembly and structure could be arranged at alternative locations along the liquid path conduits 749/762, and/or could include different types of valves and/or fluid path assemblies. For example, the valve assemblies may be disposed adjacent the liquid outlet 746, or at other locations along the conduits 749/762.

Such embodiments including structure that may allow for the reverse flow of liquid through the device 712 such that the liquid flowing in the reverse direction does not flow through the filter structure 250 may allow for the performance of certain procedures and/or operations, such as aspirating liquid from a patient, etc. without the risk of fouling of the filter structure 250 with the liquid being aspirated.

Figure 17:
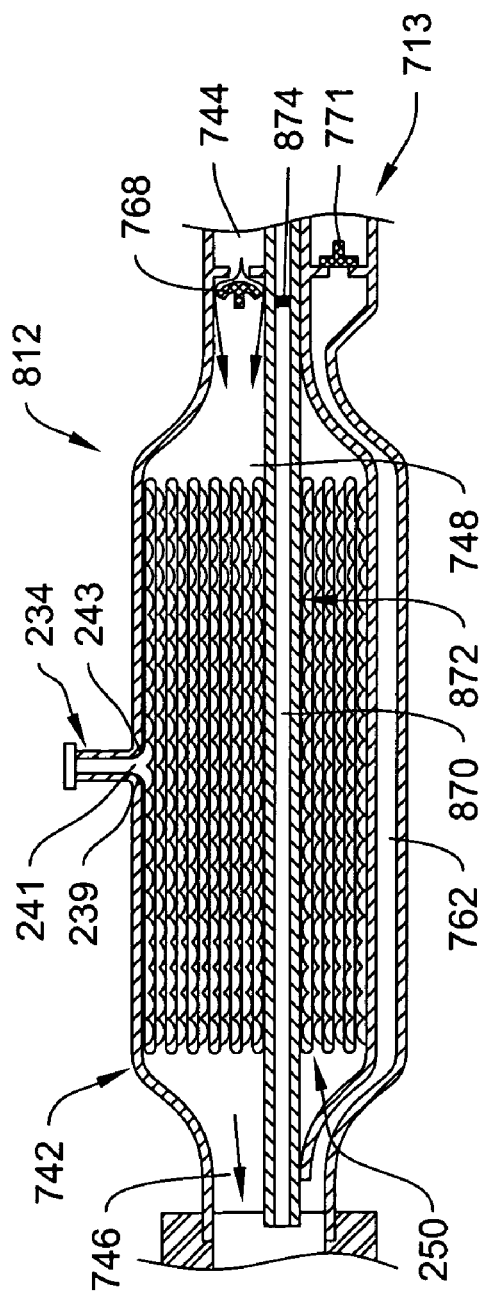
FIG. 17 is a partial cross-sectional side view of another example embodiment of a gas removal device similar to the one shown in FIG. 15, including a flow return system, and also including a device lumen.

FIG. 17 shows another alternative embodiment of a gas removal device 812, similar to that shown in FIGS. 15 and 16, wherein like reference numbers indicate similar structure. For example, the filter structure 250 and arrangement is substantially similar to the embodiment shown in FIGS. 15 and 16 (which are similar to the filter structure 250 in FIGS. 6–8). Additionally, the structure that may allow for the reverse flow of liquid through the device 812 such that the liquid flowing in the reverse direction does not flow through the filter structure 250 is substantially similar to like numbered structures shown in FIGS. 15 and 16, with a few structural differences, as indicated in the Figures.

However, in this embodiment, the device 812 further includes a conduit 870 extending through at least a portion of the chamber 748 within the housing 742, the conduit 870 extending from adjacent the liquid inlet 744 to adjacent the liquid outlet 746, and being configured to receive, for example, an elongated medical device. For example, the conduit 870 may be similar in structure and configuration to the conduit 370 described above with reference to FIG. 10. Additionally, one or more sealing structures 874 can be disposed within the lumen 872 of the conduit 870, such as the sealing structures described above with reference to FIG. 10.

FIGS. 18–20 are useful in describing another example embodiment of a gas removal device 912. Refer now to FIG. 20, which is a partial cross-sectional view taken along a vertical line perpendicular to a longitudinal axis of the gas removal device 912 (for example, a view similar to cross sectional view of the device 112 shown in FIG. 3). Similar to the devices described above, the device 912 includes a housing 942 defining a chamber 948 disposed at least partially between a liquid inlet and a liquid outlet. Although not shown in this view of the device 912, the inlet and outlet are substantially similar to those shown in the other embodiments disclosed herein. A gas filter structure 950 is disposed within the chamber 948.

With reference to FIGS. 18 and 19, the filter structure 950 is also substantially similar to the other embodiments described herein in that it includes a first gas permeable membrane layer 952 spaced from a second gas permeable membrane layer 954 to form a gas collection space 956 disposed between the two layers 952/954. The layers 952/954 each include an inner surface 951 and an outer surface 953, and the inner surfaces 951 at least partially define the bounds of the gas collection space 956, and the outer surfaces 953 at least partially define a contact area and/or liquid flow space 957 for liquid passing within the device 912. The filter structure 950 can also include one or more spacer layers 958 (i.e., permeate spacer layer) disposed within the gas collection space 956, for example, to aid in maintaining the gas collection space open. Additionally, the filter structure 950 can also include one or more spacer layers 960 (i.e., flow spacer layer) disposed within the liquid flow space 957, for example along the outer surfaces 953 of one or both of the membrane layers 952/954. The spacer layer 960 can aid in maintaining the liquid flow space 957 open by keeping the outer surfaces 953 of the two membrane layers 952/954 separate from each other and/or appropriately spaced from other structures.

The gas collection space 956 is placed in fluid communication with a gas outlet 934 using a construction similar to that shown in the embodiment shown in FIGS. 6–8. More specifically, gas outlet 934 defines one or more openings 941 in the wall of the housing 942, and fluid communication between the gas collection space 956 and the gas outlet 934 is provided through the opening 941 by attaching the gas permeable membrane layers 952/954 to the housing 942 in such a manner as to allow for such fluid communication. For example, the first layer 952 may be attached to the housing 942 along a first side of the opening 941, for example at attachment point 939, and the second layer 954 may be attached to the housing 942 along a second side of the opening 941, for example at attachment point 943. This arrangement thereby provides for fluid communication between the gas collection space 956 and the gas outlet 934. The materials, structure, size and construction of these structures can be in general accordance with the construction of similar elements discussed in the other embodiments disclosed herein.

However, in this embodiment, the filter structure 950 is oriented in the housing 942 in a folded manner, rather than in a coiled and/or spiral manner as shown in the embodiments above. More particularly, in the embodiment shown, the membrane layers 952/954 are folded along fold lines to create multiple levels and/or stages and/or layers of the membrane layers 952/954—most of which, in the embodiment shown, are generally about as long as the cavity 948 is wide. Likewise, because the membrane layers 952/954 at least partially define the gas collection space 956 and the liquid flow space 957, multiple levels and/or stages and/or layers of the gas collection space 956 and the liquid flow space 957 are also created. This type of folded configuration may allow for a filter structure 950 to have a sufficient amount of surface area for contact with liquid flowing through the device, while reducing the amount of space required by the filter structure 950. In at least some embodiments, the filter structure 950 may fill substantially the entire cross sectional area of at least a portion of the chamber 948. Such an arrangement may allow for the efficient use of space, and also may be adapted to facilitate contact between the liquid being degassed and at least a portion of the filter structure 950 (i.e., the liquid cannot pass through the device without passing through at least a portion of the filter structure.).

It should also be noted that in this embodiment, the housing is shown as a generally elongated structure having a generally rectangular cross section that is adapted to accommodate the folded shape of the filter structure 950. However, as discussed above, the housing may take other forms or shapes, for example, to accommodate other filter structures.

Reference is now made to FIG. 21, which shows another example embodiment of a gas removal device 1012. The device 1012 is substantially similar to the embodiment shown in FIGS. 6–8, and as discussed above, wherein like reference numerals indicate similar structure. For example, the filter structure 250 and arrangement is substantially similar to the embodiment shown in FIGS. 6–8.

However, this embodiment includes a gas outlet 1034 that includes a negative pressure and/or vacuum creating structure 1080 directly attached thereto. The vacuum creating structure 1080 can be adapted to apply vacuum pressure to the gas outlet 1034 which is in fluid communication with the gas collection space 256. As discussed above, such vacuum may facilitate removal of dissolved gasses from the liquid according to Henry's Law. Any of a broad variety of vacuum creating structures generally known in the art may be used, for example, a pump, syringe, bulb, or the like. In this embodiment, the vacuum creating structure 1080 is directly connected to the gas outlet 1034, and in at least some embodiments, is of unitary construction with the gas outlet 1034 and/or the housing 42 of the device 1012. For example, in the device 1012 shown, the vacuum creating structure 1080 is a syringe like structure mounted onto, and in some respects, of unitary construction with the housing 42. The structure 1080 includes a lumen 1082 defined by a portion 1031 of the housing 42 and an outer wall structure 1030. A plunger member 1084 is disposed within the lumen 1082. The plunger member 1084 can be manipulated to apply a vacuum pressure on the gas outlet 1034, and therefore to the gas collection space 256.

Reference is now made to FIGS. 22–23A, which illustrate another example embodiment of a gas removal device 1112. Similar to the devices discussed above, the device 1112 includes a housing 42 defining a liquid inlet 44, a liquid outlet 46, and a chamber 48 disposed at least partially between the inlet 44 and outlet 46. However, in this embodiment, the device 1112 includes a different gas filter structure 1150 disposed within the chamber 48.

In the embodiment shown, the filter structure 1150 includes a plurality of hollow tubular members and/or fibers 1152 made of a gas permeable membrane material. The fibers can be made of the same type of membrane material as discussed in the embodiments above, but would be hollow fiber members 1152 each including a lumen 1154 which defines a plurality of liquid flow spaces 1156. The plurality of fiber members 1152 each includes a first end 1161 and a second end 1163. The fiber members 1152 are held in place at their first ends 1161 and their second ends 1163 within the chamber 48 by first and second liquid tight seals 1190/1191 that are disposed between the ends 1161/1163 of each of the fiber members 1152 and the interior surface of the lumen defined by the cavity 48. The first and second seals 1190/1191 can include, for example, a potting resin that fills the voids between the fiber members 1152, and bonds to the interior surface of the cavity 48 to form a fluid tight seal once hardened or cured. The potting resin can comprise, for example, a multicomponent (resin and hardener component) thermosetting or UV-curable resin, such as for example, silicone, urethane or epoxy, all of which will provide secure attachment of the fiber members 1152 within the cavity 48, as well as insuring a fluid tight seal around the fiber members 1152 and against the interior surface of the cavity 48. In at least some embodiments, the material would be FDA grade.

As seen best in the cross-sectional view of FIG. 23, the fluid tight seals 1190/1191 (seal 1190 is depicted in FIG. 23 are closely formed around the external surfaces of the fiber members 1152 and, if present, the conduit 1138, which is more fully described below. As seen best in the cross-sectional view of FIG. 23A, the fiber members 1152 and, if present, the conduit 1138 extend freely between the first and second fluid tight seals 1190/1191. Alternatively, intermediate supports and/or baffles can be provided between the first and second fluid tight seals 1190/1191. The first and second fluid tight seals 1190/1191, along with the interior surface of the chamber 48, define a sealed gas collection space 1156 within the housing 42. The gas collection space 1156 is in fluid communication with the gas outlet 1134. In the embodiment shown, fluid communication between the gas collection space 1156 the gas outlet 1134 is provided by a conduit 1138 extending within the housing, the conduit 1138 connecting and in fluid communication with the gas collection space 1156 the gas outlet 1134. In the embodiment shown, the conduit 1138 is a hollow tubular member having a wall defining a lumen 1140 therein that provides fluid communication between the gas collection space 1156 and the gas outlet 1134. One or more opening 1141 is defined in the wall of the tubular member 1138 to expose the lumen 1140 therein for fluid communication between the gas collection space 1156 and the lumen 1140. As discussed above in other embodiments, the removal of dissolved gasses present in the liquid can be additionally facilitated by use of negative pressure and/or vacuum applied to the gas collection space 1156, for example, through the gas outlet 1134.

Figure 24:
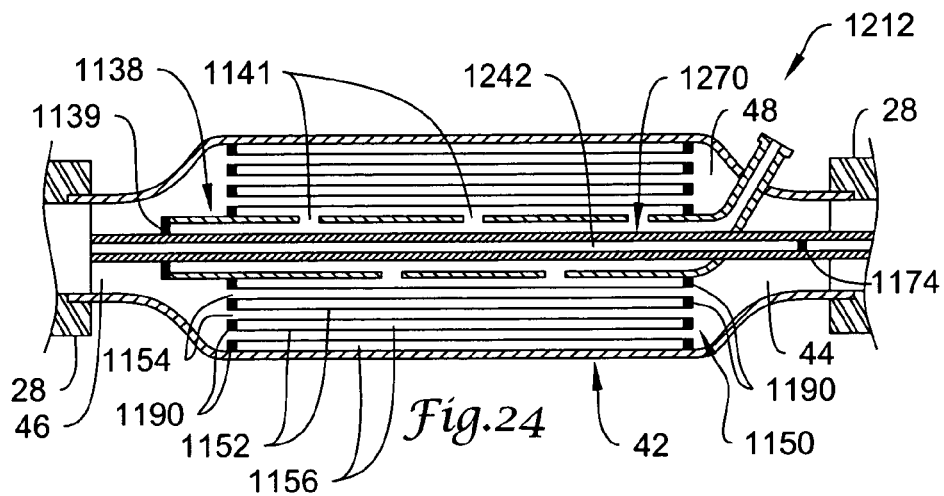
FIG. 24 is a partial cross-sectional side view of another example embodiment of a gas removal device similar to the one shown in FIG. 22, but also including a device lumen extending within the device.

FIG. 24 shows another alternative embodiment of a gas removal device 1212, similar to that shown in FIGS. 22–23, wherein like reference numbers indicate similar structure. For example, the filter structure 1150 is substantially similar to the embodiment shown in FIGS. 22–23. However, in this embodiment, the device 1212 also includes a conduit 1170 extending through at least a portion of the chamber within the housing 42, for example, as described above with reference to the devices 312/412 shown in FIGS. 10 and 11. The conduit 1170 extends from adjacent the liquid inlet 44 to adjacent the liquid outlet 46, and is configured to receive an elongated medical device. In the embodiment shown, the conduit 1170 is a tubular member defining a lumen 1242 configured for receiving and/or passing an elongated medical device there through. In the embodiment shown, the gas conduit 1138 and the medical device conduit 1170 can be coaxially disposed along at least a portion of the lengths thereof, however, this is not required.

Figure 25:
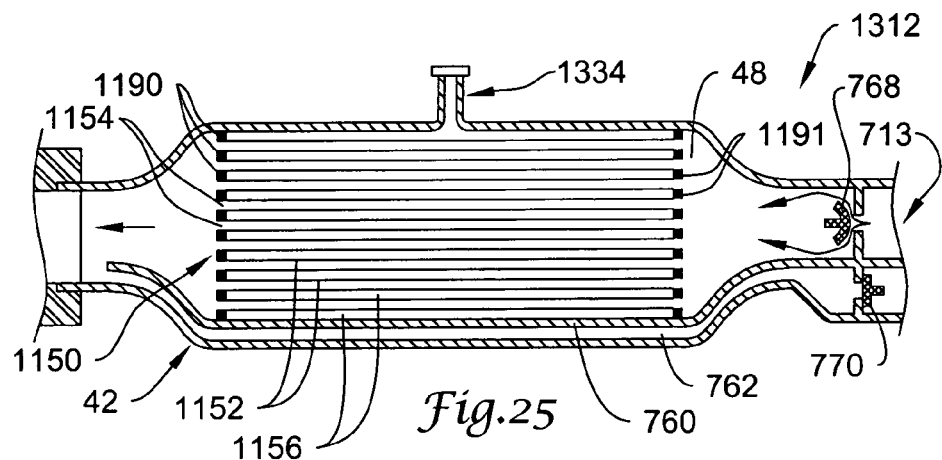
FIG. 25 is a partial cross-sectional side view of another example embodiment of a gas removal device similar to the one shown in FIG. 22, but including a side vent configuration and further including a flow return system, wherein in the embodiment shown, a check valve system is shown.

FIG. 25 shows another alternative embodiment of a gas removal device 1312, similar to that shown in FIGS. 22–23, wherein like reference numbers indicate similar structure, but including a different venting structure. Rather than including a conduit 1138 to provide fluid communication with the gas outlet 1134, as described in the embodiments of FIGS. 22–24, this embodiment provides direct fluid communication between the gas collection space 1156 and the gas outlet 1334. The gas outlet 1334 is disposed in the housing 42 in fluid communication with the gas collection space 1156. This embodiment also includes a structure that may allow for the reverse flow of liquid through the device 1312 such that the liquid flowing in the reverse direction does not flow through the filter structure 1150, for example, similar to the devices described above with reference to FIGS. 15–17, wherein like reference numbers indicate similar structure.

Figure 26:
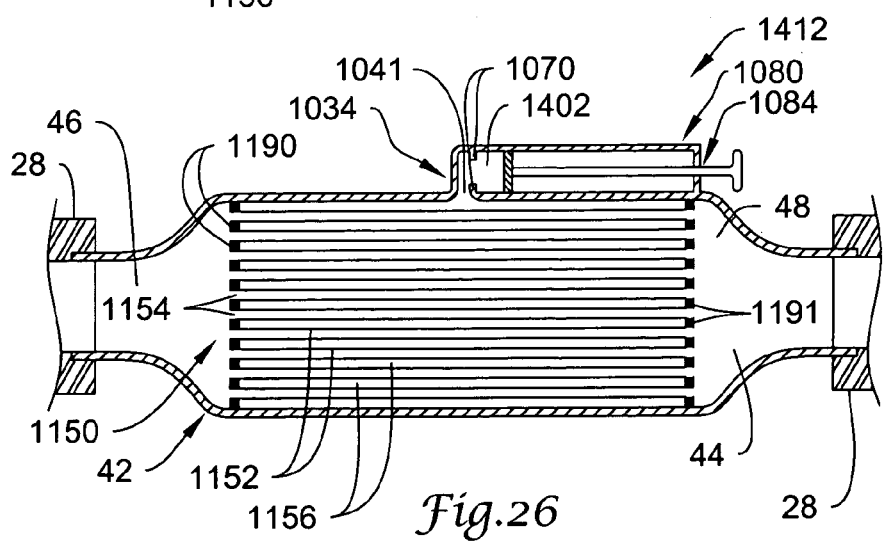
FIG. 26 is a partial cross-sectional side view of another example embodiment of a gas removal device similar to the one shown in FIG. 22, but including a side vent configuration and further including a vacuum generating device on the housing and in fluid communication with the side vent port.

FIG. 26 shows another alternative embodiment of a gas removal device 1412, similar to that shown in FIG. 25, wherein like reference numbers indicate similar structure. In this embodiment, however, the device 1412 includes a gas outlet 1034 that includes a negative pressure and/or vacuum creating structure 1080, for example, as described above in the embodiment shown in FIG. 21, wherein like reference numbers indicate similar structure.

FIG. 27 is side view of another example embodiment of a liquid delivery system 1510. The system 1510 includes some similar structure as the systems 10, 310, 510 described above with reference to FIGS. 1, 9, and 12, wherein like reference numbers indicate similar structure. For example, the catheter 25, liquid supply containers 16/18, gas removal devices 12a/12b, infusion device 20, and the other structure associated therewith can be generally the same as those described above.

However, in this embodiment, the system 1510 includes an alternative manifold construction. The manifold 1514 may still include a central or main fluid delivery lumen 1517 including one or more liquid supply ports 22/24, valves 32a/32b/32c, one or more infusion device ports 26, one or more monitoring and/or sensing devices ports 27, fluid outlet port 31, or other such structure. Additionally, the manifold may operate in generally the same manner described above. However, in this embodiment, the manifold includes a manifold body having a gas filter structure and/or device 1512 disposed within and in fluid communication with the fluid delivery lumen 1517. In at least some embodiments, as shown, the gas filter structure and/or device 1512 can be of general unitary construction with the manifold 1514. The structure of the gas filter structure and/or device 1512 incorporated into the manifold can include, for example, any of those already described herein.

It should be understood that this disclosure is, in many respects, only illustrative. Changes may be made in details, particularly in matters of shape, size, and arrangement of steps without exceeding the scope of the invention. For example, as discussed above, it will be understood by those of skill in the art and others that the gas removal devices and configurations disclosed herein may be used in any of a broad variety of fluid delivery systems and configurations, and that the specific catheter infusion systems specifically set fourth herein are given by way of example only. The invention's scope is, of course, defined in the language in which the appended claims are expressed.

What is claimed is:

1. A medical device for removing gas from a liquid to be delivered to a patient, the device comprising:
    a housing defining a chamber including a liquid inlet and a liquid outlet;
    a gas filter structure disposed within the chamber, the filter structure comprising a first gas permeable membrane layer spaced from a second gas permeable membrane layer, the first and second layers defining a gas collection space between the first and second layers, and defining a liquid flow space separated from the gas collection space by at least one of the membrane layers;
    a gas outlet in fluid communication with the gas collection space;
    a first liquid path conduit within the chamber and in fluid communication with the liquid inlet and the liquid outlet, the gas filter structure being disposed within the first liquid path conduit;
    a second liquid path conduit within the chamber and in fluid communication with the liquid inlet and the liquid outlet; and
    a valve assembly configured to allow for the flow of liquid from the liquid inlet to the liquid outlet through the first liquid path conduit while preventing the flow of liquid from the liquid inlet to the liquid outlet through the second liquid path conduit, and the valve assembly further configured to allow for the flow of liquid from the liquid outlet to the liquid inlet through the second liquid path conduit while preventing the flow of liquid from the liquid outlet to the liquid inlet through the first liquid path conduit.

2. The device of claim 1, wherein the first and second membrane layers are coiled, curved, or folded within the housing.

3. The device of claim 1, wherein the first and second membrane layers are coiled about a longitudinal axis within the housing.

4. The device of claim 1, wherein the first and second membrane layers are folded within the housing.

5. The device of claim 1, wherein the first and second membrane layers each include an inner surface defining at least a portion of the gas collection space and an outer surface defining at least a portion of the liquid flow space.

6. The device of claim 5, wherein the first and second membrane layers are coiled, curved, or folded within the housing such that at least a portion of the liquid flow space is defined between outer surfaces of the membrane layers.

7. The device of claim 1, further including a conduit extending within the housing, the conduit connecting and in fluid communication with the gas collection space and the gas outlet.

8. The device of claim 7, wherein the conduit comprises a tubular member extending within the housing, the tubular member defining a lumen that provides fluid communication between the gas collection space and the gas outlet.

9. The device of claim 8, wherein at least a portion of the tubular member extends along a longitudinal axis within the housing, and the first and second membrane layers are coiled about the tubular member along at least a portion of the longitudinal axis.

10. The device of claim 8, wherein the tubular member includes a wall defining the lumen, and one or more opening in the wall, and wherein the first gas permeable membrane layer is connected to the wall along a first side of the opening and the second gas permeable membrane layer is connected to the wall along a second side of the opening so as to provide fluid communication between the gas collection space and the lumen.

11. The device of claim 1, wherein the gas outlet comprises a gas outlet port defined in the housing.

12. The device of claim 11, wherein the gas outlet port defines one or more opening in the housing, and wherein the first gas permeable membrane layer is connected to the housing along a first side of the opening and the second gas permeable membrane layer is connected to the housing along a second side of the opening so as to provide fluid communication between the gas collection space and the gas outlet port.

13. The device of claim 1, further including a conduit extending through at least a portion of the chamber within the housing, the conduit extending from adjacent the liquid inlet to adjacent the liquid outlet, and being configured to receive an elongated medical device.

14. The device of claim 13, wherein the conduit comprises a tubular member extending within the chamber within the housing, the tubular member defining a lumen configured for receiving or passing an elongated medical device there through.

15. The device of claim 13, wherein the conduit extends to a medical device delivery port in the housing.

16. The device of claim 1, further including a conduit extending through at least a portion of the chamber within the housing, the conduit extending from a medical device delivery port in the housing to adjacent the liquid outlet, and being configured to receive an elongated medical device.

17. The device of claim 1, further including:
a first conduit extending within the housing, the conduit extending between and in fluid communication with the gas collection space and the gas outlet; and
a second conduit extending within the housing, the second conduit extending from adjacent the liquid inlet to adjacent the liquid outlet, and being configured to receive an elongated medical device.

18. The device of claim 17, wherein the first and second conduits are coaxially disposed along at least a portion of the lengths thereof.

19. The device of claim 1, wherein the filter structure further includes a gas permeable spacer layer disposed within the gas collection space.

20. The device of claim 1, wherein the filter structure further includes a liquid permeable spacer layer disposed within the liquid flow space.

21. The device of claim 1, wherein the valve assembly includes:

a first one way check valve disposed within the first liquid path conduit and allowing one-directional liquid flow from the liquid inlet to the liquid outlet through the first liquid path conduit; and
a second one way check valve disposed within the second liquid path conduit and allowing one-directional liquid flow from the liquid outlet to the liquid inlet through the second liquid path conduit.

22. The device of claim 1, wherein the device further includes a vacuum creating structure attached to the housing and in fluid communication with the gas outlet.

23. The device of claim 22, wherein the vacuum creating structure includes a structure mounted onto the housing and defining a lumen in fluid communication with the gas outlet, and a plunger member disposed within the lumen.

24. A medical device for removing gas from a liquid to be delivered to a patient, the device comprising:
a housing defining a chamber including a liquid inlet and a liquid outlet;
a filter structure disposed within the chamber, the filter structure comprising: a first gas permeable membrane layer including an inner surface and an outer surface; a gas permeable spacer layer; a second gas permeable membrane layer including an inner surface and an outer surface; and a liquid permeable spacer layer; the first and second membrane layers being connected and defining an inner gas collection space between the inner surfaces of the first and second membrane layers, and defining a liquid flow space separated from the gas collection space by at least one of the membrane layers; the gas permeable spacer layer being disposed within the gas collection space, and the liquid permeable spacer layer being disposed within the liquid flow space;
a gas outlet in fluid communication with the gas collection space;
a first liquid path conduit within the chamber and in fluid communication with the liquid inlet and the liquid outlet, the gas filter structure being disposed within the first liquid path conduit;
a second liquid path conduit within the chamber and in fluid communication with the liquid inlet and the liquid outlet; and
a valve assembly configured to allow for the flow of liquid from the liquid inlet to the liquid outlet through the first liquid path conduit while preventing the flow of liquid from the liquid inlet to the liquid outlet through the second liquid path conduit, and the valve assembly further configured to allow for the flow of liquid from the liquid outlet to the liquid inlet through the second liquid path conduit while preventing the flow of liquid from the liquid outlet to the liquid inlet through the first liquid path conduit.

25. The device of claim 24, wherein the housing and filter structure are configured such that when the liquid is introduced through the inlet port into the chamber at least some of the liquid contacts the liquid contact surface such that at least a portion of gasses present in the liquid permeate through one of the membrane layers and into the gas collection space.

26. A medical device for removing gas from a liquid to be delivered to a patient, the device comprising:
a housing defining a chamber including a liquid inlet and a liquid outlet;
a filter structure disposed within the chamber, the filter structure comprising a first gas permeable membrane layer spaced apart from a second gas permeable membrane layer, both layers including an inner surface, an outer surface, and an outer periphery, the first and second layers connected to each other along at least a portion of the outer peripheries and defining a gas collection space between the inner surfaces of the first and second layers, and defining a liquid flow space along at least a portion of the outer surface of one or both of the first and second layers;

a gas outlet in fluid communication with the gas collection space;

a first liquid path conduit within the chamber and in fluid communication with the liquid inlet and the liquid outlet, the gas filter structure being disposed within the first liquid path conduit;

a second liquid path conduit within the chamber and in fluid communication with the liquid inlet and the liquid outlet; and a valve assembly configured to allow for the flow of liquid from the liquid inlet to the liquid outlet through the first liquid path conduit while preventing the flow of liquid from the liquid inlet to the liquid outlet through the second liquid path conduit, and the valve assembly further configured to allow for the flow of liquid from the liquid outlet to the liquid inlet through the second liquid path conduit while preventing the flow of liquid from the liquid outlet to the liquid inlet through the first liquid path conduit.

27. A medical fluid delivery system for use in delivering a liquid to a patient, the system comprising:

a fluid delivery manifold including a manifold body defining a fluid delivery lumen, the manifold including one or more liquid inlet ports and one or more liquid outlet ports in selective fluid communication with the fluid delivery lumen; and a device for removing gas from the liquid, the device being configured to be connected to at least one of the ports of the manifold, the device including a housing defining a chamber including a liquid inlet and a liquid outlet; a gas filter structure disposed within the chamber, the filter structure comprising a first gas permeable membrane layer spaced from a second gas permeable membrane layer, the first and second layers defining a gas collection space between the first and second layers, and defining a liquid flow space separated from the gas collection space by at least one of the membrane layers;

a gas outlet in fluid communication with the gas collection space;

a first liquid path conduit within the chamber and in fluid communication with the liquid inlet and the liquid outlet, the gas filter structure being disposed within the first liquid path conduit;

a second liquid path conduit within the chamber and in fluid communication with the liquid inlet and the liquid outlet; and a valve assembly configured to allow for the flow of liquid from the liquid inlet to the liquid outlet through the first liquid path conduit while preventing the flow of liquid from the liquid inlet to the liquid outlet through the second liquid path conduit, and the valve assembly further configured to allow for the flow of liquid from the liquid outlet to the liquid inlet through the second liquid path conduit while preventing the flow of liquid from the liquid outlet to the liquid inlet through the first liquid path conduit.

28. A method for removing gasses from a liquid to be delivered to a patient, the method comprising:

providing a medical device for removing gas from the liquid, the device comprising:

a housing defining a chamber including a liquid inlet and a liquid outlet;

a gas filter structure disposed within the chamber, the filter structure comprising a first gas permeable membrane layer spaced from a second gas permeable membrane layer, the first and second layers defining a gas collection space between the first and second layers, and defining a liquid flow space separated from the gas collection space by at least one of the membrane layers;

a gas outlet in fluid communication with the gas collection space;

a first liquid path conduit within the chamber and in fluid communication with the liquid inlet and the liquid outlet, the gas filter structure being disposed within the first liquid path conduit;

a second liquid path conduit within the chamber and in fluid communication with the liquid inlet and the liquid outlet; and a valve assembly configured to allow for the flow of liquid from the liquid inlet to the liquid outlet through the first liquid path conduit while preventing the flow of liquid from the liquid inlet to the liquid outlet through the second liquid path conduit, and the valve assembly further configured to allow for the flow of liquid from the liquid outlet to the liquid inlet through the second liquid path conduit while preventing the flow of liquid from the liquid outlet to the liquid inlet through the first liquid path conduit;

introducing liquid into the chamber through the liquid inlet such that the liquid flows into the liquid flow space; and moving the liquid from within the liquid flow space and through the liquid outlet.

29. The method of claim 28, wherein the first and second membrane layers are coiled, curved, or folded within the housing.

30. The method of claim 28, wherein the first and second membrane layers are coiled about a longitudinal axis within the housing.

31. The method of claim 28, wherein the first and second membrane layers are folded within the housing.

32. The method of claim 28, wherein the first and second membrane layers each include an inner surface defining at least a portion of the gas collection space and an outer surface defining at least a portion of the liquid flow space.

33. The method of claim 32, wherein the first and second membrane layers are coiled, curved, or folded within the housing such that at least a portion of the liquid flow space is defined between outer surfaces of the membrane layers.

34. The method of claim 28, wherein the device further includes a conduit extending within the housing, the conduit extending between and in fluid communication with the gas collection space and the gas outlet.

35. The method of claim 34, wherein the conduit comprises a tubular member extending within the housing, the tubular member defining a lumen that provides fluid communication between the gas collection space and the gas outlet.

36. The method of claim 35, wherein at least a portion of the tubular member extends along a longitudinal axis within the housing, and the first and second membrane layers are coiled about the tubular member along at least a portion of the longitudinal axis.

37. The method of claim 35, wherein the tubular member includes a wall defining the lumen, and one or more opening in the wall, and wherein the first gas permeable membrane layer is connected to the wall along a first side of the opening and the second gas permeable membrane layer is connected to the wall along a second side of the opening so as to provide fluid communication between the gas collection space and the lumen.

38. The method of claim 28, wherein the gas outlet comprises a gas outlet port defined in the housing.

39. The method of claim 38, wherein the gas outlet port defines one or more opening in the housing, and wherein the first gas permeable membrane layer is connected to the housing along a first side of the opening and the second gas permeable membrane layer is connected to the housing along a second side of the opening so as to provide fluid communication between the gas collection space and the gas outlet port.

40. The method of claim 28, wherein the device further includes a conduit extending through at least a portion of the chamber within the housing, the conduit extending from adjacent the liquid inlet to adjacent the liquid outlet, and being configured to receive an elongated medical device.

41. The method of claim 40, wherein the conduit comprises a tubular member extending within the chamber within the housing, the tubular member defining a lumen configured for receiving or passing an elongated medical device there through.

42. The method of claim 40, wherein the conduit extends to a medical device delivery port in the housing.

43. The method of claim 28, wherein the device further includes a conduit extending through at least a portion of the chamber within the housing, the conduit extending from a medical device delivery port in the housing to adjacent the liquid outlet, and being configured to receive an elongated medical device.

44. The method of claim 28, wherein the device further includes:
a first conduit extending within the housing, the conduit extending between and in fluid communication with the gas collection space and the gas outlet; and
a second conduit extending within the housing, the second conduit extending from adjacent the liquid inlet to adjacent the liquid outlet, and being configured to receive an elongated medical device.

45. The method of claim 44, wherein the first and second conduits are coaxially disposed along at least a portion of the lengths thereof.

46. The method of claim 28, wherein the filter structure further includes a gas permeable spacer layer disposed within the gas collection space.

47. The method of claim 28, wherein the filter structure further includes a liquid permeable spacer layer disposed within the liquid flow space.

48. The method of claim 28, wherein the valve assembly includes:
a first one way check valve disposed within the first liquid path conduit and allowing one-directional liquid flow from the liquid inlet to the liquid outlet through the first liquid path conduit; and
a second one way check valve disposed within the second liquid path conduit and allowing one-directional liquid flow from the liquid outlet to the liquid inlet through the second liquid path conduit.

49. The method of claim 28, wherein the device further includes a vacuum creating structure attached to the housing and fluid communication with the gas outlet.

50. The method of claim 49, wherein the vacuum creating structure includes a structure mounted onto the housing and defining a lumen in fluid communication with the gas outlet, and a plunger member disposed within the lumen.

51. A manifold for use in delivering a liquid to a patient, the manifold comprising:
a manifold body defining a fluid delivery lumen, the manifold body including a plurality of liquid inlet ports in fluid communication with the lumen and one or more liquid outlet ports, the manifold body also including a gas filter structure disposed within the fluid delivery lumen, the gas filter structure comprising:
a first gas permeable membrane layer and a second gas permeable membrane layer, the first and second layers forming a gas collection space between the first and second layers, and defining a liquid flow space separated from the gas collection space by at least one of the membrane layers; and
a gas outlet in fluid communication with the gas collection space.

52. A manifold for use in delivering a liquid to a patient, the manifold comprising:
a manifold body defining a fluid delivery lumen having an inner surface, the manifold body including a plurality of liquid inlet ports in fluid communication with the lumen and one or more liquid outlet ports, the manifold body also including a gas filter structure disposed within the fluid delivery lumen, the gas filter structure comprising:
a plurality of hollow tubular members made of a gas permeable membrane material disposed within the lumen, each of the tubular members having a first end and a second end;
a first liquid tight seal between the first end of each of the tubular members and the interior surface of the lumen;
a second liquid tight seal between the second end of each of the tubular members and the interior surface of the lumen, wherein a gas collection space is defined by the first and second liquid tight seals; and
a gas outlet in fluid communication with the gas collection space.

53. A medical device for removing gas from a liquid to be delivered to a patient, the device comprising:
a housing defining a chamber defining an inner surface and including a liquid inlet and a liquid outlet;
a gas filter structure disposed within the chamber, the filter structure comprising:
a plurality of hollow tubular members made of a gas permeable membrane material disposed within the chamber, each of the tubular members having a first end and a second end;
a first liquid tight seal between the first end of each of the tubular members and the interior surface of the chamber;
a second liquid tight seal between the second end of each of the tubular members and the interior surface of the chamber, wherein a gas collection space is defined by the first and second liquid tight seals;
a gas outlet port extending through the housing; and
a conduit extending within the housing, the conduit connecting and in fluid communication with the gas collection space and the gas outlet, wherein the conduit comprises a tubular member extending within the chamber, the tubular member defining a lumen that provides fluid communication between the gas collection space and the gas outlet.

54. The device of claim 53, wherein at least a portion of the tubular member extends along a longitudinal axis within the housing and within the gas collection space.

55. The device of claim 53, further including a second conduit extending within the housing, the second conduit extending from adjacent the liquid inlet to adjacent the liquid outlet, and being configured to receive an elongated medical device.

56. The device of claim 55, wherein the conduit and the second conduit are coaxially disposed along at least a portion of the lengths thereof.

57. A medical device for removing gas from a liquid to be delivered to a patient, the device comprising:
 a housing defining a chamber defining an inner surface and including a liquid inlet and a liquid outlet;
 a gas filter structure disposed within the chamber, the filter structure comprising:
  a plurality of hollow tubular members made of a gas permeable membrane material disposed within the chamber, each of the tubular members having a first end and a second end;
  a first liquid tight seal between the first end of each of the tubular members and the interior surface of the chamber; and
  a second liquid tight seal between the second end of each of the tubular members and the interior surface of the chamber, wherein a gas collection space is defined by the first and second liquid tight seals;
 a gas outlet in fluid communication with the gas collection space; and
 a vacuum creating structure attached to the housing and in fluid communication with the gas outlet, wherein the vacuum creating structure is permanently mounted onto or of uniform construction with the housing and defines a lumen in fluid communication with the gas outlet.

58. The device of claim 57, wherein the vacuum creating structure includes a plunger member disposed within the lumen.

59. A medical device for removing gas from a liquid to be delivered to a patient, the device comprising:
 a housing defining a chamber defining an inner surface and including a liquid inlet and a liquid outlet;
 a first liquid path conduit within the chamber and in fluid communication with the liquid inlet and the liquid outlet, the first liquid path conduit defining a lumen having an inner surface;
 a second liquid path conduit within the chamber and in fluid communication with the liquid inlet and the liquid outlet;
 a valve assembly configured to allow for the flow of liquid from the liquid inlet to the liquid outlet through the first liquid path conduit while preventing the flow of liquid from the liquid inlet to the liquid outlet through the second liquid path conduit, and the valve assembly further configured to allow for the flow of liquid from the liquid outlet to the liquid inlet through the second liquid path conduit while preventing the flow of liquid from the liquid outlet to the liquid inlet through the first liquid path conduit; and
 a gas filter structure disposed within the first liquid path conduit, the filter structure comprising:
  a plurality of hollow tubular members made of a gas permeable membrane material disposed within the lumen, each of the tubular members having a first end and a second end;
  a first liquid tight seal between the first end of each of the tubular members and the inner surface of the lumen;
  a second liquid tight seal between the second end of each of the tubular members and the inner surface of the lumen, wherein a gas collection space is defined by the first and second liquid tight seals; and
  a gas outlet in fluid communication with the gas collection space.

60. The device of claim 59, wherein the valve assembly includes:
 a first one way check valve disposed within the first liquid path conduit and allowing one-directional liquid flow from the liquid inlet to the liquid outlet through the first liquid path conduit; and
 a second one way check valve disposed within the second liquid path conduit and allowing one-directional liquid flow from the liquid outlet to the liquid inlet through the second liquid path conduit.

* * * * *

UNITED STATES PATENT AND TRADEMARK OFFICE
CERTIFICATE OF CORRECTION

PATENT NO. : 7,097,690 B2
APPLICATION NO. : 10/684215
DATED : August 29, 2006
INVENTOR(S) : Kathryn M. Usher et al.

It is certified that error appears in the above-identified patent and that said Letters Patent is hereby corrected as shown below:

Column 8
Line 17, delete "al", and insert therefor -- at --.

Column 16
Line 52, after "collection space" and before "open", insert -- 956 --.

Column 18
Line 44, after "FIG. 23", insert --) --.

Signed and Sealed this

Twelfth Day of December, 2006

JON W. DUDAS
*Director of the United States Patent and Trademark Office*